United States Patent
Alexander

(10) Patent No.: US 12,310,853 B2
(45) Date of Patent: *May 27, 2025

(54) SYSTEMS AND METHODS FOR TREATING CARDIAC DYSFUNCTION

(71) Applicant: EDWARDS LIFESCIENCES CORPORATION, Irvine, CA (US)

(72) Inventor: Miles D. Alexander, Menlo Park, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/199,420

(22) Filed: May 19, 2023

(65) Prior Publication Data

US 2023/0285149 A1    Sep. 14, 2023

Related U.S. Application Data

(63) Continuation of application No. 16/997,634, filed on Aug. 19, 2020, now Pat. No. 11,690,720, which is a
(Continued)

(30) Foreign Application Priority Data

Sep. 28, 2014  (CN) .......................... 201420564242.9
Sep. 28, 2014  (CN) .......................... 201420564806.9
Sep. 28, 2014  (CN) .......................... 201420564809.2

(51) Int. Cl.
*A61F 2/24* (2006.01)
*A61B 17/00* (2006.01)
(Continued)

(52) U.S. Cl.
CPC ...... *A61F 2/2487* (2013.01); *A61B 17/12036* (2013.01); *A61B 17/12122* (2013.01);
(Continued)

(58) Field of Classification Search
CPC .... A61F 2/2487; A61F 2/9525; A61F 2/2436; A61F 2/9522; A61F 2210/0014;
(Continued)

(56) References Cited

U.S. PATENT DOCUMENTS 3,409,013 A    11/1968 Berry
3,472,230 A    10/1969 Fogarty
(Continued)

FOREIGN PATENT DOCUMENTS

CA         2304325 A1   10/2000
CN       204169959 U    2/2015
(Continued)

OTHER PUBLICATIONS

Andersen, et al., "Transluminal implantation of artificial heart valves. Description of a new expandable aortic valve and initial results with implantation by catheter technique in closed chest pigs."European Heart Journal (1992), 13, 704-708
(Continued)

*Primary Examiner* — Jacqueline Woznicki
(74) *Attorney, Agent, or Firm* — Thomas C. Richardson

(57) ABSTRACT

A system for treating cardiac dysfunction can include an expandable device for insertion into a heart, a foot configured to contact a portion of the heart, a support frame, and a membrane coupled to the support frame. The support frame can include a plurality of radially expandable struts each having a first free end configured to extend beyond the foot and a second end coupled to the foot. The plurality of radially expandable struts can include a plurality of staggered stops, and each of the stops can be positioned on a respective one of the struts proximal to the first free end of the respective one of the struts. Method for treating cardiac dysfunction can include implanting the systems described herein into a chamber of the heart.

20 Claims, 13 Drawing Sheets

Related U.S. Application Data continuation of application No. 15/506,562, filed as application No. PCT/US2015/050827 on Sep. 18, 2015, now Pat. No. 10,751,183.

(51) Int. Cl.
*A61B 17/12* (2006.01)
*A61F 2/95* (2013.01)
*A61B 17/064* (2006.01)

(52) U.S. Cl.
CPC .. *A61B 17/12145* (2013.01); *A61B 17/12168* (2013.01); *A61F 2/9525* (2020.05); *A61B 2017/0053* (2013.01); *A61B 2017/0641* (2013.01); *A61B 2017/1205* (2013.01); *A61F 2/2436* (2013.01); *A61F 2/9522* (2020.05); *A61F 2210/0014* (2013.01); *A61F 2220/0041* (2013.01); *A61F 2230/0093* (2013.01)

(58) Field of Classification Search
CPC ...... A61F 2220/0041; A61F 2220/0075; A61F 2230/0093; A61B 17/12122; A61B 17/12145; A61B 2560/0456; A61B 2217/002; A61B 2560/04; A61B 2017/1205; A61B 17/12136
See application file for complete search history.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,739,402 A | 6/1973 | Cooley et al. |
| 3,755,823 A | 9/1973 | Hancock |
| 3,874,388 A | 4/1975 | King et al. |
| 4,007,743 A | 2/1977 | Blake |
| 4,035,849 A | 7/1977 | Angell et al. |
| 4,056,854 A | 11/1977 | Boretos et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,425,908 A | 1/1984 | Simon |
| 4,453,545 A | 6/1984 | Inoue |
| 4,470,157 A | 9/1984 | Love |
| 4,477,930 A | 10/1984 | Totten et al. |
| 4,490,859 A | 1/1985 | Black et al. |
| 4,535,483 A | 8/1985 | Klawitter et al. |
| 4,536,893 A | 8/1985 | Parravicini |
| 4,553,545 A | 11/1985 | Maass et al. |
| 4,574,803 A | 3/1986 | Storz |
| 4,588,404 A | 5/1986 | Lapeyre |
| 4,592,340 A | 6/1986 | Boyles |
| 4,605,407 A | 8/1986 | Black et al. |
| 4,612,011 A | 9/1986 | Kautzky |
| 4,619,246 A | 10/1986 | Molgaard-Nielsen et al. |
| 4,643,732 A | 2/1987 | Pietsch et al. |
| 4,655,771 A | 4/1987 | Wallsten |
| 4,685,446 A | 8/1987 | Choy |
| 4,692,164 A | 9/1987 | Dzemeshkevich et al. |
| 4,710,192 A | 12/1987 | Liotta et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,830,003 A | 5/1989 | Wolff et al. |
| 4,832,055 A | 5/1989 | Palestrant |
| 4,851,001 A | 7/1989 | Taheri |
| 4,856,516 A | 8/1989 | Hillstead |
| 4,865,600 A | 9/1989 | Carpentier et al. |
| 4,878,495 A | 11/1989 | Grayzel |
| 4,878,906 A | 11/1989 | Lindemann et al. |
| 4,883,458 A | 11/1989 | Shiber |
| 4,917,089 A | 4/1990 | Sideris |
| 4,922,905 A | 5/1990 | Strecker |
| 4,966,604 A | 10/1990 | Reiss |
| 4,979,939 A | 12/1990 | Shiber |
| 4,983,165 A | 1/1991 | Loiterman |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,104,399 A | 4/1992 | Lazarus |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,192,301 A | 3/1993 | Kamiya et al. |
| 5,192,314 A | 3/1993 | Daskalakis |
| 5,232,446 A | 8/1993 | Arney |
| 5,258,000 A | 11/1993 | Gianturco |
| 5,266,073 A | 11/1993 | Wall |
| 5,282,847 A | 2/1994 | Trescony et al. |
| 5,295,958 A | 3/1994 | Shturman |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,375,612 A | 12/1994 | Cottenceau et al. |
| 5,385,156 A | 1/1995 | Oliva |
| 5,389,087 A | 2/1995 | Miraki |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,415,667 A | 5/1995 | Frater |
| 5,425,744 A | 6/1995 | Fagan et al. |
| 5,433,727 A | 7/1995 | Sideris |
| 5,443,446 A | 8/1995 | Shturman |
| 5,451,235 A | 9/1995 | Lock et al. |
| 5,480,424 A | 1/1996 | Cox |
| 5,496,277 A | 3/1996 | Termin et al. |
| 5,500,014 A | 3/1996 | Quijano et al. |
| 5,527,337 A | 6/1996 | Stack et al. |
| 5,527,338 A | 6/1996 | Purdy |
| 5,545,209 A | 8/1996 | Roberts et al. |
| 5,545,214 A | 8/1996 | Stevens |
| 5,549,621 A | 8/1996 | Bessler et al. |
| 5,549,665 A | 8/1996 | Vesely et al. |
| 5,551,435 A | 9/1996 | Sramek |
| 5,554,185 A | 9/1996 | Block et al. |
| 5,571,175 A | 11/1996 | Vanney et al. |
| 5,578,069 A | 11/1996 | Miner, II |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,634,936 A | 6/1997 | Linden et al. |
| 5,634,942 A | 6/1997 | Chevillon et al. |

(56) References Cited

U.S. PATENT DOCUMENTS

| | | |
|---|---|---|
| 5,639,274 A | 6/1997 | Fischell et al. |
| 5,647,870 A | 7/1997 | Kordis et al. |
| 5,665,115 A | 9/1997 | Cragg |
| 5,697,382 A | 12/1997 | Love et al. |
| 5,702,343 A | 12/1997 | Alferness |
| 5,702,441 A | 12/1997 | Zhou |
| 5,709,707 A | 1/1998 | Lock et al. |
| 5,716,417 A | 2/1998 | Girard et al. |
| 5,728,068 A | 3/1998 | Leone et al. |
| 5,746,734 A | 5/1998 | Dormandy, Jr. et al. |
| 5,749,890 A | 5/1998 | Shaknovich |
| 5,756,476 A | 5/1998 | Epstein et al. |
| 5,758,664 A | 6/1998 | Campbell et al. |
| 5,769,812 A | 6/1998 | Stevens et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,800,508 A | 9/1998 | Goicoechea et al. |
| 5,800,517 A | 9/1998 | Anderson et al. |
| 5,829,447 A | 11/1998 | Stevens et al. |
| 5,833,682 A | 11/1998 | Amplatz et al. |
| 5,833,698 A | 11/1998 | Hinchliffe et al. |
| 5,836,968 A | 11/1998 | Simon et al. |
| 5,840,081 A | 11/1998 | Andersen et al. |
| 5,843,170 A | 12/1998 | Ahn |
| 5,855,597 A | 1/1999 | Jayaraman |
| 5,855,601 A | 1/1999 | Bessler et al. |
| 5,855,602 A | 1/1999 | Angell |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,906,619 A | 5/1999 | Olson et al. |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,063 A | 7/1999 | Khosravi |
| 5,925,076 A | 7/1999 | Inoue |
| 5,928,260 A | 7/1999 | Chin et al. |
| 5,957,949 A | 9/1999 | Leonhardt et al. |
| 5,961,440 A | 10/1999 | Schweich, Jr. et al. |
| 5,961,539 A | 10/1999 | Northrup, III et al. |
| 5,968,068 A | 10/1999 | Dehdashtian et al. |
| 5,984,917 A | 11/1999 | Fleischman et al. |
| 6,024,096 A | 2/2000 | Buckberg |
| 6,024,756 A | 2/2000 | Huebsch et al. |
| 6,027,525 A | 2/2000 | Suh et al. |
| 6,036,720 A | 3/2000 | Abrams et al. |
| 6,042,607 A | 3/2000 | Williamson, IV et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,086,612 A | 7/2000 | Jansen |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,113,631 A | 9/2000 | Jansen |
| 6,125,852 A | 10/2000 | Stevens et al. |
| 6,132,438 A | 10/2000 | Fleischman et al. |
| 6,132,473 A | 10/2000 | Williams et al. |
| 6,142,973 A | 11/2000 | Carleton et al. |
| 6,152,144 A | 11/2000 | Lesh et al. |
| 6,155,968 A | 12/2000 | Wilk |
| 6,156,027 A | 12/2000 | West |
| 6,161,543 A | 12/2000 | Cox et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,193,731 B1 | 2/2001 | Oppelt et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,221,092 B1 | 4/2001 | Koike et al. |
| 6,221,104 B1 | 4/2001 | Buckberg et al. |
| 6,230,714 B1 | 5/2001 | Alferness et al. |
| 6,231,561 B1 | 5/2001 | Frazier et al. |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,251,093 B1 | 6/2001 | Valley et al. |
| 6,258,021 B1 | 7/2001 | Wilk |
| 6,264,630 B1 | 7/2001 | Mickley et al. |
| 6,267,772 B1 | 7/2001 | Mulhauser et al. |
| 6,287,339 B1 | 9/2001 | Vazquez et al. |
| 6,290,674 B1 | 9/2001 | Roue et al. |
| 6,296,656 B1 | 10/2001 | Bolduc et al. |
| 6,299,637 B1 | 10/2001 | Shaolian et al. |
| 6,302,906 B1 | 10/2001 | Goecoechea et al. |
| 6,306,141 B1 | 10/2001 | Jervis |
| 6,312,446 B1 | 11/2001 | Huebsch et al. |
| 6,312,465 B1 | 11/2001 | Griffin et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,350,277 B1 | 2/2002 | Kocur |
| 6,355,052 B1 | 3/2002 | Neuss et al. |
| 6,358,277 B1 | 3/2002 | Duran |
| 6,360,749 B1 | 3/2002 | Jayaraman |
| 6,364,896 B1 | 4/2002 | Addis |
| 6,379,372 B1 | 4/2002 | Dehdashtian et al. |
| 6,387,042 B1 | 5/2002 | Herrero |
| 6,406,420 B1 | 6/2002 | McCarthy et al. |
| 6,419,669 B1 | 7/2002 | Frazier et al. |
| 6,425,916 B1 | 7/2002 | Garrison et al. |
| 6,436,088 B2 | 8/2002 | Frazier et al. |
| 6,440,164 B1 | 8/2002 | Di Matteo et al. |
| 6,450,171 B1 | 9/2002 | Buckberg et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,146 B1 | 11/2002 | Alferness et al. |
| 6,482,228 B1 | 11/2002 | Norred |
| 6,488,704 B1 | 12/2002 | Connelly et al. |
| 6,506,204 B2 | 1/2003 | Mazzocchi |
| 6,508,756 B1 | 1/2003 | Kung et al. |
| 6,511,496 B1 | 1/2003 | Huter et al. |
| 6,527,800 B1 | 3/2003 | McGuckin, Jr. et al. |
| 6,527,979 B2 | 3/2003 | Constantz |
| 6,537,198 B1 | 3/2003 | Vidlund et al. |
| 6,540,782 B1 | 4/2003 | Snyders |
| 6,551,303 B1 | 4/2003 | Van Tassel et al. |
| 6,569,196 B1 | 5/2003 | Vesely |
| 6,572,643 B1 | 6/2003 | Gharibadeh |
| 6,575,959 B1 | 6/2003 | Sarge et al. |
| 6,582,462 B1 | 6/2003 | Andersen et al. |
| 6,586,414 B2 | 7/2003 | Haque et al. |
| 6,592,608 B2 | 7/2003 | Fisher et al. |
| 6,605,112 B1 | 8/2003 | Moll et al. |
| 6,610,088 B1 | 8/2003 | Gabbay |
| 6,613,013 B2 | 9/2003 | Haarala et al. |
| 6,622,730 B2 | 9/2003 | Ekvall et al. |
| 6,629,534 B1 | 10/2003 | Goar et al. |
| 6,645,199 B1 | 11/2003 | Jenkins et al. |
| 6,652,555 B1 | 11/2003 | VanTassel et al. |
| 6,676,698 B2 | 1/2004 | McGuckin, Jr. et al. |
| 6,681,773 B2 | 1/2004 | Murphy et al. |
| 6,685,627 B2 | 2/2004 | Jayaraman |
| 6,695,878 B2 | 2/2004 | McGuckin, Jr. et al. |
| 6,702,763 B2 | 3/2004 | Murphy et al. |
| 6,712,836 B1 | 3/2004 | Berg et al. |

(56) References Cited

U.S. PATENT DOCUMENTS

| | | |
|---|---|---|
| 6,716,207 B2 | 4/2004 | Farnholtz |
| 6,729,356 B1 | 5/2004 | Baker et al. |
| 6,730,108 B2 | 5/2004 | Van Tassel et al. |
| 6,730,118 B2 | 5/2004 | Spenser et al. |
| 6,733,525 B2 | 5/2004 | Yang et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,776,754 B1 | 8/2004 | Wilk |
| 6,780,200 B2 | 8/2004 | Jansen |
| 6,790,229 B1 | 9/2004 | Berreklouw |
| 6,790,230 B2 | 9/2004 | Beyersdorf et al. |
| 6,830,584 B1 | 12/2004 | Seguin |
| 6,852,076 B2 | 2/2005 | Nikolic et al. |
| 6,875,231 B2 | 4/2005 | Anduiza et al. |
| 6,887,192 B1 | 5/2005 | Whayne et al. |
| 6,893,460 B2 | 5/2005 | Spenser et al. |
| 6,908,481 B2 | 6/2005 | Cribier |
| 6,951,534 B2 | 10/2005 | Girard et al. |
| 6,959,711 B2 | 11/2005 | Murphy et al. |
| 6,974,476 B2 | 12/2005 | McGuckin, Jr. et al. |
| 6,994,093 B2 | 2/2006 | Murphy et al. |
| 7,018,406 B2 | 3/2006 | Seguin et al. |
| 7,144,363 B2 | 12/2006 | Pai et al. |
| 7,172,551 B2 | 2/2007 | Leasure |
| 7,175,660 B2 | 2/2007 | Cartledge et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,279,007 B2 | 10/2007 | Nikolic et al. |
| 7,303,526 B2 | 12/2007 | Sharkey et al. |
| 7,318,278 B2 | 1/2008 | Zhang et al. |
| 7,320,665 B2 | 1/2008 | Vijay |
| 7,374,571 B2 | 5/2008 | Pease et al. |
| 7,381,210 B2 | 6/2008 | Zarbatany et al. |
| 7,381,219 B2 | 6/2008 | Salahieh et al. |
| 7,393,360 B2 | 7/2008 | Spenser et al. |
| 7,399,271 B2 | 7/2008 | Khairkhahan et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,485,088 B2 | 2/2009 | Murphy et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,530,998 B1 | 5/2009 | Starkey |
| 7,553,324 B2 | 6/2009 | Andreas et al. |
| 7,569,062 B1 | 8/2009 | Kuehn et al. |
| 7,579,381 B2 | 8/2009 | Dove |
| 7,582,051 B2 | 9/2009 | Khairkhahan et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,674,222 B2 | 3/2010 | Nikolic et al. |
| 7,704,222 B2 | 4/2010 | Wilk et al. |
| 7,736,327 B2 | 6/2010 | Wilk et al. |
| 7,748,389 B2 | 7/2010 | Salahieh et al. |
| 7,753,949 B2 | 7/2010 | Lamphere et al. |
| 7,758,491 B2 | 7/2010 | Buckner et al. |
| 7,762,943 B2 | 7/2010 | Khairkhahan |
| 7,806,919 B2 | 10/2010 | Bloom et al. |
| 7,824,325 B2 | 11/2010 | Dubi |
| 7,824,443 B2 | 11/2010 | Salahieh et al. |
| 7,837,727 B2 | 11/2010 | Goetz et al. |
| 7,862,500 B2 | 1/2011 | Khairkhahan et al. |
| 7,887,477 B2 | 2/2011 | Nikolic et al. |
| 7,892,281 B2 | 2/2011 | Seguin et al. |
| 7,897,086 B2 | 3/2011 | Khairkhahan et al. |
| 7,914,569 B2 | 3/2011 | Nguyen et al. |
| 7,914,575 B2 | 3/2011 | Guyenot et al. |
| 7,938,767 B2 | 5/2011 | Evans et al. |
| 7,959,672 B2 | 6/2011 | Salahieh et al. |
| 7,972,378 B2 | 7/2011 | Tabor et al. |
| 7,976,455 B2 | 7/2011 | Khairkhahan |
| 7,981,151 B2 | 7/2011 | Rowe |
| 7,993,258 B2 | 8/2011 | Feld et al. |
| 7,993,392 B2 | 8/2011 | Righini et al. |
| 7,993,394 B2 | 8/2011 | Hariton et al. |
| 8,007,992 B2 | 8/2011 | Tian et al. |
| 8,016,877 B2 | 9/2011 | Seguin et al. |
| 8,029,556 B2 | 10/2011 | Rowe |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,092,521 B2 | 1/2012 | Figulla et al. |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,932 B2 | 5/2012 | Bourang |
| 8,167,934 B2 | 5/2012 | Styrc et al. |
| 8,182,530 B2 | 5/2012 | Huber |
| 8,192,478 B2 | 6/2012 | Khairkhahan et al. |
| 8,206,437 B2 | 6/2012 | Bonhoeffer et al. |
| 8,216,174 B2 | 7/2012 | Wilk et al. |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,236,045 B2 | 8/2012 | Benichou et al. |
| 8,246,671 B2 | 8/2012 | Khairkhahan |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,257,428 B2 | 9/2012 | Khairkhahan et al. |
| 8,287,584 B2 | 10/2012 | Salahieh et al. |
| 8,313,525 B2 | 11/2012 | Tuval et al. |
| 8,317,858 B2 | 11/2012 | Straubinger et al. |
| 8,323,335 B2 | 12/2012 | Rowe et al. |
| 8,337,541 B2 | 12/2012 | Quadri et al. |
| 8,353,953 B2 | 1/2013 | Giannetti et al. |
| 8,377,114 B2 | 2/2013 | Khairkhahan et al. |
| 8,382,653 B2 | 2/2013 | Dubi et al. |
| 8,388,672 B2 | 3/2013 | Khairkhahan et al. |
| 8,398,537 B2 | 3/2013 | Khairkhahan et al. |
| 8,398,704 B2 | 3/2013 | Straubinger et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,416,643 B2 | 4/2013 | Magee |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,460,370 B2 | 6/2013 | Zakay |
| 8,470,023 B2 | 6/2013 | Eidenschink et al. |
| 8,470,028 B2 | 6/2013 | Thornton et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,491,650 B2 | 7/2013 | Wiemeyer et al. |
| 8,500,622 B2 | 8/2013 | Lipperman et al. |
| 8,500,733 B2 | 8/2013 | Watson |
| 8,500,790 B2 | 8/2013 | Khairkhahan |
| 8,500,795 B2 | 8/2013 | Khairkhahan et al. |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,529,430 B2 | 9/2013 | Nikolic et al. |
| 8,562,663 B2 | 10/2013 | Mearns et al. |
| 8,579,963 B2 | 11/2013 | Tabor |
| 8,579,964 B2 | 11/2013 | Lane et al. |
| 8,591,570 B2 | 11/2013 | Revuelta et al. |
| 8,617,236 B2 | 12/2013 | Paul et al. |

(56) References Cited

U.S. PATENT DOCUMENTS

| | | |
|---|---|---|
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,657,873 B2 | 2/2014 | Khairkhahan et al. |
| 8,668,733 B2 | 3/2014 | Haug et al. |
| 8,672,827 B2 | 3/2014 | Nikolic et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,758,432 B2 | 6/2014 | Solem |
| 8,764,818 B2 | 7/2014 | Gregg |
| 8,764,848 B2 | 7/2014 | Callaghan et al. |
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,242 B2 | 7/2014 | Kermode et al. |
| 8,790,387 B2 | 7/2014 | Nguyen et al. |
| 8,795,357 B2 | 8/2014 | Yohanan et al. |
| 8,808,356 B2 | 8/2014 | Braido et al. |
| 8,827,892 B2 | 9/2014 | Nikolic et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,911,455 B2 | 12/2014 | Quadri et al. |
| 8,926,693 B2 | 1/2015 | Duffy et al. |
| 8,926,694 B2 | 1/2015 | Costello |
| 8,931,159 B2 | 1/2015 | Hillukka |
| 8,939,960 B2 | 1/2015 | Rosenman et al. |
| 8,945,209 B2 | 2/2015 | Bonyuet et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,375 B2 | 3/2015 | Garde et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,017,394 B2 | 4/2015 | Khairkhahan |
| 9,028,545 B2 | 5/2015 | Taylor |
| 9,034,032 B2 | 5/2015 | McLean et al. |
| 9,039,597 B2 | 5/2015 | Kermode et al. |
| 9,055,937 B2 | 6/2015 | Rowe et al. |
| 9,066,801 B2 | 6/2015 | Kovalsky et al. |
| 9,078,660 B2 | 7/2015 | Boutillette et al. |
| 9,078,749 B2 | 7/2015 | Lutter et al. |
| 9,078,751 B2 | 7/2015 | Naor |
| 9,125,738 B2 | 9/2015 | Figulla et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,192,496 B2 | 11/2015 | Robinson |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,295,551 B2 | 3/2016 | Straubinger et al. |
| 9,332,992 B2 | 5/2016 | Alexander |
| 9,332,993 B2 | 5/2016 | Kermode et al. |
| 9,364,327 B2 | 6/2016 | Kermode et al. |
| 9,445,897 B2 | 9/2016 | Bishop et al. |
| 9,456,877 B2 | 10/2016 | Weitzner et al. |
| 9,592,123 B2 | 3/2017 | Nikolic et al. |
| 9,681,968 B2 | 6/2017 | Goetz et al. |
| 9,687,345 B2 | 6/2017 | Rabito et al. |
| 9,700,329 B2 | 7/2017 | Metzger et al. |
| 9,700,411 B2 | 7/2017 | Klima et al. |
| 9,724,083 B2 | 8/2017 | Quadri et al. |
| 9,730,790 B2 | 8/2017 | Quadri et al. |
| 9,730,791 B2 | 8/2017 | Ratz et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 10,004,599 B2 | 6/2018 | Rabito et al. |
| 10,117,744 B2 | 11/2018 | Ratz et al. |
| 10,179,044 B2 | 1/2019 | Ratz et al. |
| 10,219,897 B2 | 3/2019 | Essinger et al. |
| 10,307,147 B2 | 6/2019 | Khairkhahan et al. |
| 10,350,065 B2 | 7/2019 | Quadri |
| 10,350,066 B2 | 7/2019 | Cooper et al. |
| 10,376,363 B2 | 8/2019 | Quadri et al. |
| 10,555,809 B2 | 2/2020 | Hastings et al. |
| 10,575,951 B2 | 3/2020 | Johnson et al. |
| 10,583,000 B2 | 3/2020 | Ratz et al. |
| 10,639,146 B2 | 5/2020 | Quadri et al. |
| 10,695,177 B2 | 6/2020 | Hariton et al. |
| 10,758,344 B2 | 9/2020 | Hariton et al. |
| 11,406,499 B2 | 8/2022 | Zhang et al. |
| 11,452,598 B2 | 9/2022 | Essinger et al. |
| 11,672,658 B2 | 6/2023 | Hariton et al. |
| 11,690,720 B2 * | 7/2023 | Alexander ....... A61B 17/12036 623/1.11 |
| 11,701,225 B2 | 7/2023 | Hammer et al. |
| 11,864,771 B2 * | 1/2024 | Alexander ....... A61B 17/12172 |
| 11,903,829 B1 | 2/2024 | Ma et al. |
| 2001/0014800 A1 | 8/2001 | Frazier et al. |
| 2001/0021872 A1 | 9/2001 | Bailey et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0055767 A1 | 5/2002 | Forde et al. |
| 2002/0055775 A1 | 5/2002 | Carpentier et al. |
| 2002/0056461 A1 | 5/2002 | Jayaraman |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0173842 A1 | 11/2002 | Buchanan |
| 2002/0183604 A1 | 12/2002 | Gowda et al. |
| 2002/0183827 A1 | 12/2002 | Derus et al. |
| 2002/0188170 A1 | 12/2002 | Santamore et al. |
| 2003/0012337 A1 | 1/2003 | Fewster et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0050694 A1 | 3/2003 | Yang et al. |
| 2003/0057156 A1 | 3/2003 | Peterson et al. |
| 2003/0078671 A1 | 4/2003 | Lesniak et al. |
| 2003/0100939 A1 | 5/2003 | Yodfat et al. |
| 2003/0105384 A1 | 6/2003 | Sharkey et al. |
| 2003/0105517 A1 | 6/2003 | White et al. |
| 2003/0109770 A1 | 6/2003 | Sharkey et al. |
| 2003/0120333 A1 | 6/2003 | Ouriel et al. |
| 2003/0120337 A1 | 6/2003 | Van Tassel et al. |
| 2003/0130729 A1 | 7/2003 | Paniagua et al. |

(56) References Cited

U.S. PATENT DOCUMENTS

| | | |
|---|---|---|
| 2003/0135230 A1 | 7/2003 | Massey et al. |
| 2003/0149333 A1 | 8/2003 | Alferness |
| 2003/0149422 A1 | 8/2003 | Muller |
| 2003/0158570 A1 | 8/2003 | Ferrazzi |
| 2003/0158597 A1 | 8/2003 | Quiachon et al. |
| 2003/0176914 A1 | 9/2003 | Rabkin et al. |
| 2003/0181928 A1 | 9/2003 | Vidlund et al. |
| 2003/0181942 A1 | 9/2003 | Sutton et al. |
| 2003/0199971 A1 | 10/2003 | Tower et al. |
| 2003/0212429 A1 | 11/2003 | Keegan et al. |
| 2003/0212454 A1 | 11/2003 | Scott et al. |
| 2003/0220667 A1 | 11/2003 | van der Burg et al. |
| 2003/0220683 A1 | 11/2003 | Minasian et al. |
| 2003/0225445 A1 | 12/2003 | Derus et al. |
| 2003/0229265 A1 | 12/2003 | Girard et al. |
| 2004/0002626 A1 | 1/2004 | Feld et al. |
| 2004/0034366 A1 | 2/2004 | van der Burg et al. |
| 2004/0039436 A1 | 2/2004 | Spenser et al. |
| 2004/0044361 A1 | 3/2004 | Frazier et al. |
| 2004/0049210 A1 | 3/2004 | VanTassel et al. |
| 2004/0054394 A1 | 3/2004 | Lee |
| 2004/0064014 A1 | 4/2004 | Melvin et al. |
| 2004/0092858 A1 | 5/2004 | Wilson et al. |
| 2004/0117009 A1 | 6/2004 | Cali et al. |
| 2004/0122090 A1 | 6/2004 | Lipton |
| 2004/0127935 A1 | 7/2004 | VanTassel et al. |
| 2004/0133062 A1 | 7/2004 | Pai et al. |
| 2004/0133263 A1 | 7/2004 | Dusbabek et al. |
| 2004/0133273 A1 | 7/2004 | Cox |
| 2004/0136992 A1 | 7/2004 | Burton et al. |
| 2004/0172042 A1 | 9/2004 | Suon et al. |
| 2004/0186511 A1 | 9/2004 | Stephens et al. |
| 2004/0186563 A1 | 9/2004 | Lobbi |
| 2004/0186565 A1 | 9/2004 | Schreck |
| 2004/0210307 A1 | 10/2004 | Khairkhahan |
| 2004/0215230 A1 | 10/2004 | Frazier et al. |
| 2004/0215325 A1 | 10/2004 | Penn et al. |
| 2004/0220610 A1 | 11/2004 | Kreidler et al. |
| 2004/0225353 A1 | 11/2004 | McGuckin et al. |
| 2004/0236411 A1 | 11/2004 | Sarac et al. |
| 2004/0243170 A1 | 12/2004 | Suresh et al. |
| 2004/0260331 A1 | 12/2004 | D'Aquanni et al. |
| 2004/0260346 A1 | 12/2004 | Overall et al. |
| 2004/0260389 A1 | 12/2004 | Case et al. |
| 2004/0267086 A1 | 12/2004 | Anstadt et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0033398 A1 | 2/2005 | Seguin |
| 2005/0038470 A1 | 2/2005 | van der Burg et al. |
| 2005/0043708 A1 | 2/2005 | Gleeson et al. |
| 2005/0065548 A1 | 3/2005 | Marino et al. |
| 2005/0075727 A1 | 4/2005 | Wheatley |
| 2005/0085826 A1 | 4/2005 | Nair et al. |
| 2005/0090887 A1 | 4/2005 | Pryor |
| 2005/0096498 A1 | 5/2005 | Houser et al. |
| 2005/0096738 A1 | 5/2005 | Cali et al. |
| 2005/0107872 A1 | 5/2005 | Mensah et al. |
| 2005/0113811 A1 | 5/2005 | Houser et al. |
| 2005/0113861 A1 | 5/2005 | Corcoran et al. |
| 2005/0124849 A1 | 6/2005 | Barbut et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137691 A1 | 6/2005 | Salahieh et al. |
| 2005/0137698 A1 | 6/2005 | Salahieh et al. |
| 2005/0142180 A1 | 6/2005 | Bisgaier et al. |
| 2005/0154252 A1 | 7/2005 | Sharkey et al. |
| 2005/0159811 A1 | 7/2005 | Lane |
| 2005/0177180 A1 | 8/2005 | Kaganov et al. |
| 2005/0182486 A1 | 8/2005 | Gabbay |
| 2005/0187620 A1 | 8/2005 | Pai et al. |
| 2005/0197716 A1 | 9/2005 | Sharkey et al. |
| 2005/0203614 A1 | 9/2005 | Forster et al. |
| 2005/0203617 A1 | 9/2005 | Forster et al. |
| 2005/0216052 A1 | 9/2005 | Mazzocchi et al. |
| 2005/0216079 A1 | 9/2005 | MaCoviak |
| 2005/0228434 A1 | 10/2005 | Amplatz et al. |
| 2005/0234546 A1 | 10/2005 | Nugent et al. |
| 2005/0256532 A1 | 11/2005 | Nayak et al. |
| 2005/0277981 A1 | 12/2005 | Maahs et al. |
| 2005/0277983 A1 | 12/2005 | Saadat et al. |
| 2005/0283218 A1 | 12/2005 | Williams |
| 2005/0288766 A1 | 12/2005 | Plain et al. |
| 2006/0014998 A1 | 1/2006 | Sharkey et al. |
| 2006/0019888 A1 | 1/2006 | Zhou |
| 2006/0020327 A1 | 1/2006 | Lashinski et al. |
| 2006/0025800 A1 | 2/2006 | Suresh |
| 2006/0025857 A1 | 2/2006 | Bergheim et al. |
| 2006/0030881 A1 | 2/2006 | Sharkey et al. |
| 2006/0058872 A1 | 3/2006 | Salahieh et al. |
| 2006/0063970 A1 | 3/2006 | Raman et al. |
| 2006/0069430 A9 | 3/2006 | Rahdert et al. |
| 2006/0079736 A1 | 4/2006 | Chin et al. |
| 2006/0095115 A1 | 5/2006 | Bladillah et al. |
| 2006/0116692 A1 | 6/2006 | Ward |
| 2006/0135947 A1 | 6/2006 | Soltesz et al. |
| 2006/0136043 A1 | 6/2006 | Cully et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0167334 A1 | 7/2006 | Anstadt et al. |
| 2006/0173524 A1 | 8/2006 | Salahieh et al. |
| 2006/0173537 A1 | 8/2006 | Yang et al. |
| 2006/0195134 A1 | 8/2006 | Crittenden |
| 2006/0195183 A1 | 8/2006 | Navia et al. |
| 2006/0199995 A1 | 9/2006 | Vijay |
| 2006/0212110 A1 | 9/2006 | Osborne et al. |
| 2006/0229491 A1 | 10/2006 | Sharkey et al. |
| 2006/0229719 A1 | 10/2006 | Marquez et al. |
| 2006/0241334 A1 | 10/2006 | Dubi et al. |
| 2006/0241745 A1 | 10/2006 | Solem |
| 2006/0259124 A1 | 11/2006 | Matsuoka et al. |
| 2006/0259135 A1 | 11/2006 | Navia et al. |
| 2006/0259137 A1 | 11/2006 | Artof et al. |
| 2006/0264980 A1 | 11/2006 | Khairkhahan et al. |
| 2006/0276684 A1 | 12/2006 | Speziali |
| 2006/0276874 A1 | 12/2006 | Wilson et al. |
| 2006/0281965 A1 | 12/2006 | Khairkhahan et al. |
| 2006/0293745 A1 | 12/2006 | Carpentier et al. |
| 2007/0005131 A1 | 1/2007 | Taylor |
| 2007/0010877 A1 | 1/2007 | Salahieh et al. |
| 2007/0027534 A1 | 2/2007 | Bergheim et al. |
| 2007/0043435 A1 | 2/2007 | Seguin et al. |
| 2007/0050021 A1 | 3/2007 | Johnson |
| 2007/0066863 A1 | 3/2007 | Rafiee et al. |
| 2007/0088431 A1 | 4/2007 | Bourang et al. |
| 2007/0100432 A1 | 5/2007 | Case et al. |
| 2007/0100439 A1 | 5/2007 | Cangialosi et al. |
| 2007/0112422 A1 | 5/2007 | Dehdashtian |
| 2007/0129753 A1 | 6/2007 | Quinn et al. |
| 2007/0129794 A1 | 6/2007 | Realyvasquez |
| 2007/0135826 A1 | 6/2007 | Zaver et al. |
| 2007/0135889 A1 | 6/2007 | Moore et al. |
| 2007/0142906 A1 | 6/2007 | Figulla et al. |
| 2007/0156224 A1 | 7/2007 | Cioanta et al. |
| 2007/0161846 A1 | 7/2007 | Nikolic et al. |
| 2007/0162048 A1 | 7/2007 | Quinn et al. |
| 2007/0203503 A1 | 8/2007 | Salahieh et al. |
| 2007/0203575 A1 | 8/2007 | Forster et al. |
| 2007/0213578 A1 | 9/2007 | Khairkhahan et al. |
| 2007/0213813 A1 | 9/2007 | Von Segesser et al. |
| 2007/0213815 A1 | 9/2007 | Khairkhahan et al. |
| 2007/0255394 A1 | 11/2007 | Ryan |
| 2007/0270931 A1 | 11/2007 | Leanna et al. |
| 2007/0270943 A1 | 11/2007 | Solem et al. |
| 2008/0015717 A1 | 1/2008 | Griffin et al. |
| 2008/0021546 A1 | 1/2008 | Patz et al. |
| 2008/0045778 A1 | 2/2008 | Lichtenstein et al. |
| 2008/0065011 A1 | 3/2008 | Marchand et al. |
| 2008/0071133 A1 | 3/2008 | Dubi |
| 2008/0071134 A1 | 3/2008 | Dubi et al. |

(56) References Cited

U.S. PATENT DOCUMENTS

| | | |
|---|---|---|
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097581 A1 | 4/2008 | Shanley |
| 2008/0114442 A1 | 5/2008 | Mitchell et al. |
| 2008/0125853 A1 | 5/2008 | Bailey et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0161910 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0208332 A1 | 8/2008 | Lamphere et al. |
| 2008/0221384 A1 | 9/2008 | Chi Sing et al. |
| 2008/0221672 A1 | 9/2008 | Lamphere et al. |
| 2008/0228205 A1 | 9/2008 | Sharkey et al. |
| 2008/0228254 A1 | 9/2008 | Ryan |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0293996 A1 | 11/2008 | Evans et al. |
| 2008/0300672 A1 | 12/2008 | Kassab et al. |
| 2008/0319254 A1 | 12/2008 | Nikolic et al. |
| 2009/0005863 A1 | 1/2009 | Goetz et al. |
| 2009/0054723 A1 | 2/2009 | Khairkhahan et al. |
| 2009/0054968 A1 | 2/2009 | Bonhoeffer et al. |
| 2009/0054974 A1 | 2/2009 | McGuckin, Jr. et al. |
| 2009/0062601 A1 | 3/2009 | Khairkhahan et al. |
| 2009/0076598 A1 | 3/2009 | Salahieh et al. |
| 2009/0112050 A1 | 4/2009 | Farnan et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182413 A1 | 7/2009 | Burkart et al. |
| 2009/0187063 A1 | 7/2009 | Khairkhahan |
| 2009/0188964 A1 | 7/2009 | Orlov |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0228093 A1 | 9/2009 | Taylor et al. |
| 2009/0234443 A1 | 9/2009 | Ottma et al. |
| 2009/0240320 A1 | 9/2009 | Tuval et al. |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2010/0016958 A1 | 1/2010 | St. Goar et al. |
| 2010/0022821 A1 | 1/2010 | Dubi et al. |
| 2010/0030256 A1 | 2/2010 | Dubrul et al. |
| 2010/0049313 A1 | 2/2010 | Alon et al. |
| 2010/0057185 A1 | 3/2010 | Melsheimer et al. |
| 2010/0069852 A1 | 3/2010 | Kelley |
| 2010/0114305 A1 | 5/2010 | Kang et al. |
| 2010/0121132 A1 | 5/2010 | Nikolic et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0191326 A1 | 7/2010 | Alkhatib |
| 2010/0204781 A1 | 8/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0262231 A1 | 10/2010 | Tuval et al. |
| 2010/0274227 A1 | 10/2010 | Khairkhahan et al. |
| 2010/0305685 A1 | 12/2010 | Millwee et al. |
| 2010/0312333 A1 | 12/2010 | Navia et al. |
| 2011/0015616 A1 | 1/2011 | Straubinger et al. |
| 2011/0015729 A1 | 1/2011 | Jimenez et al. |
| 2011/0021864 A1 | 1/2011 | Criscione et al. |
| 2011/0046712 A1 | 2/2011 | Melsheimer et al. |
| 2011/0092761 A1 | 4/2011 | Almog et al. |
| 2011/0098525 A1 | 4/2011 | Kermode et al. |
| 2011/0137397 A1 | 6/2011 | Chau et al. |
| 2011/0178362 A1 | 7/2011 | Evans et al. |
| 2011/0178597 A9 | 7/2011 | Navia et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0238159 A1 | 9/2011 | Guyenot et al. |
| 2011/0257461 A1 | 10/2011 | Lipperman et al. |
| 2011/0264196 A1 | 10/2011 | Savage et al. |
| 2011/0264198 A1 | 10/2011 | Murray, III et al. |
| 2011/0264204 A1 | 10/2011 | Khairkhahan |
| 2011/0288634 A1 | 11/2011 | Tuval et al. |
| 2011/0313515 A1 | 12/2011 | Quadri et al. |
| 2011/0319989 A1 | 12/2011 | Lane et al. |
| 2012/0022639 A1 | 1/2012 | Hacohen et al. |
| 2012/0035722 A1 | 2/2012 | Tuval |
| 2012/0041257 A1 | 2/2012 | Stankus et al. |
| 2012/0041550 A1 | 2/2012 | Salahieh et al. |
| 2012/0046741 A1 | 2/2012 | Tuval et al. |
| 2012/0046742 A1 | 2/2012 | Tuval et al. |
| 2012/0078360 A1 | 3/2012 | Rafiee |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0215303 A1 | 8/2012 | Quadri et al. |
| 2012/0245604 A1 | 9/2012 | Tegzes |
| 2012/0271398 A1 | 10/2012 | Essinger et al. |
| 2012/0283823 A1 | 11/2012 | Bonhoeffer et al. |
| 2012/0290062 A1 | 11/2012 | McNamara et al. |
| 2012/0296418 A1 | 11/2012 | Bonyuet et al. |
| 2012/0310328 A1 | 12/2012 | Olson et al. |
| 2012/0310336 A1 | 12/2012 | Figulla et al. |
| 2012/0330408 A1 | 12/2012 | Hillukka et al. |
| 2013/0006294 A1 | 1/2013 | Kashkarov et al. |
| 2013/0035759 A1 | 2/2013 | Gross et al. |
| 2013/0073035 A1 | 3/2013 | Tuval et al. |
| 2013/0079869 A1 | 3/2013 | Straubinger et al. |
| 2013/0090677 A1 | 4/2013 | Evans et al. |
| 2013/0165735 A1 | 6/2013 | Khairkhahan et al. |
| 2013/0190861 A1 | 7/2013 | Chau et al. |
| 2013/0190862 A1 | 7/2013 | Pintor et al. |
| 2013/0197622 A1 | 8/2013 | Mitra et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0274595 A1 | 10/2013 | Kermode et al. |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0100651 A1 | 4/2014 | Kheradvar et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |

(56) References Cited

U.S. PATENT DOCUMENTS

| | | |
|---|---|---|
| 2014/0180271 A1 | 6/2014 | Johnson et al. |
| 2014/0194981 A1 | 7/2014 | Menk et al. |
| 2014/0207231 A1 | 7/2014 | Hacohen et al. |
| 2014/0214157 A1 | 7/2014 | Bortlein et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0243966 A1 | 8/2014 | Garde et al. |
| 2014/0257467 A1 | 9/2014 | Lane et al. |
| 2014/0277390 A1 | 9/2014 | Ratz et al. |
| 2014/0277412 A1 | 9/2014 | Bortlein et al. |
| 2014/0277422 A1 | 9/2014 | Ratz et al. |
| 2014/0277426 A1 | 9/2014 | Dakin et al. |
| 2014/0277427 A1 | 9/2014 | Ratz et al. |
| 2014/0296624 A1 | 10/2014 | Kermode et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0331475 A1* | 11/2014 | Duffy ................ A61F 2/243 29/446 |
| 2014/0336754 A1 | 11/2014 | Gurskis et al. |
| 2014/0343356 A1 | 11/2014 | Nikolic et al. |
| 2014/0343669 A1 | 11/2014 | Lane et al. |
| 2014/0343670 A1 | 11/2014 | Bakis et al. |
| 2014/0345109 A1 | 11/2014 | Grant et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364941 A1 | 12/2014 | Edmiston et al. |
| 2014/0364943 A1 | 12/2014 | Conklin |
| 2014/0371789 A1 | 12/2014 | Hariton et al. |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray et al. |
| 2015/0005863 A1 | 1/2015 | Para |
| 2015/0018944 A1 | 1/2015 | O'Connell et al. |
| 2015/0039083 A1 | 2/2015 | Rafiee |
| 2015/0142103 A1 | 5/2015 | Vidlund |
| 2015/0148731 A1 | 5/2015 | McNamara et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0209144 A1 | 7/2015 | Khairkhahan |
| 2015/0265405 A1 | 9/2015 | Boutillette et al. |
| 2015/0272737 A1 | 10/2015 | Dale et al. |
| 2015/0297346 A1 | 10/2015 | Duffy et al. |
| 2015/0297381 A1 | 10/2015 | Essinger et al. |
| 2015/0335429 A1 | 11/2015 | Morriss et al. |
| 2015/0351903 A1 | 12/2015 | Morriss et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0262892 A1 | 9/2016 | Kermode et al. |
| 2016/0279386 A1 | 9/2016 | Dale et al. |
| 2016/0302924 A1 | 10/2016 | Boutillette et al. |
| 2016/0310267 A1 | 10/2016 | Zeng et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367821 A1 | 12/2017 | Landon et al. |
| 2017/0367823 A1 | 12/2017 | Hariton et al. |
| 2018/0021129 A1 | 1/2018 | Peterson et al. |
| 2018/0055629 A1 | 3/2018 | Oba et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |
| 2018/0116790 A1 | 5/2018 | Ratz et al. |
| 2019/0008639 A1 | 1/2019 | Landon et al. |
| 2019/0008640 A1 | 1/2019 | Cooper et al. |
| 2019/0060072 A1 | 2/2019 | Zeng |
| 2019/0262129 A1 | 8/2019 | Cooper et al. |
| 2020/0000579 A1 | 1/2020 | Manash et al. |
| 2020/0108225 A1 | 4/2020 | Jamal et al. |
| 2020/0345494 A1 | 11/2020 | Srinimukesh et al. |
| 2020/0352718 A1 | 11/2020 | Rowe et al. |
| 2021/0145576 A1 | 5/2021 | Becerra et al. |
| 2021/0378817 A1 | 12/2021 | Nia et al. |
| 2021/0386544 A1 | 12/2021 | Cooper et al. |
| 2022/0142777 A1 | 5/2022 | Scheinblum et al. |
| 2022/0287836 A1 | 9/2022 | Landon et al. |
| 2022/0346993 A1 | 11/2022 | Srinimukesh et al. |
| 2023/0000624 A1 | 1/2023 | Okabe et al. |
| 2023/0200980 A1 | 6/2023 | Peterson et al. |
| 2023/0218391 A1 | 7/2023 | Dass et al. |
| 2023/0380963 A1 | 11/2023 | Kaufman et al. |
| 2023/0390052 A1 | 12/2023 | Okafor et al. |
| 2023/0404753 A1 | 12/2023 | Luong et al. |
| 2024/0008978 A1 | 1/2024 | Nawalakhe et al. |

FOREIGN PATENT DOCUMENTS

| | | |
|---|---|---|
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1171059 A1 | 1/2002 |
| EP | 1239901 A1 | 9/2002 |
| EP | 1255510 A1 | 11/2002 |
| EP | 1259194 A1 | 11/2002 |
| EP | 1369098 A1 | 12/2003 |
| EP | 1469797 A1 | 10/2004 |
| EP | 1472996 A1 | 11/2004 |
| EP | 1474032 A2 | 11/2004 |
| EP | 1570809 A1 | 9/2005 |
| EP | 1653888 A2 | 5/2006 |
| EP | 1849440 A1 | 10/2007 |
| EP | 1935377 A1 | 6/2008 |
| EP | 2124826 A1 | 12/2009 |
| EP | 2168536 A1 | 3/2010 |
| EP | 2413842 A1 | 2/2012 |
| EP | 2446915 A1 | 5/2012 |
| EP | 2082690 B1 | 6/2012 |
| EP | 2745805 A1 | 6/2014 |
| EP | 2749254 A1 | 7/2014 |

(56) References Cited

FOREIGN PATENT DOCUMENTS

| | | |
|---|---|---|
| EP | 2750630 A1 | 7/2014 |
| EP | 2777616 A1 | 9/2014 |
| EP | 2777617 A1 | 9/2014 |
| EP | 2918249 A2 | 9/2015 |
| EP | 2948103 A2 | 12/2015 |
| EP | 2967858 A2 | 1/2016 |
| EP | 3037064 A1 | 6/2016 |
| EP | 3046511 A2 | 7/2016 |
| EP | 3057541 A1 | 8/2016 |
| EP | 3075354 A2 | 10/2016 |
| EP | 3139864 A1 | 3/2017 |
| EP | 3142603 A1 | 3/2017 |
| EP | 3184083 A1 | 6/2017 |
| EP | 3294220 A1 | 3/2018 |
| EP | 3417813 A1 | 12/2018 |
| EP | 3570779 A1 | 11/2019 |
| FR | 2788217 A1 | 7/2000 |
| GB | 1264471 A | 2/1972 |
| GB | 1315844 A | 5/1973 |
| GB | 2056023 A | 3/1981 |
| GB | 2398245 A | 8/2004 |
| SU | 1271508 A1 | 11/1986 |
| WO | 9116041 A1 | 10/1991 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9803213 A1 | 1/1998 |
| WO | 9829057 A1 | 7/1998 |
| WO | 9933414 A1 | 7/1999 |
| WO | 9940964 A1 | 8/1999 |
| WO | 9947075 A1 | 9/1999 |
| WO | 0041652 A1 | 7/2000 |
| WO | 0047139 A1 | 8/2000 |
| WO | 0061034 A1 | 10/2000 |
| WO | 0236048 A1 | 5/2002 |
| WO | 0245710 A1 | 6/2002 |
| WO | 02087481 A1 | 11/2002 |
| WO | 03047468 A1 | 6/2003 |
| WO | 03092554 A1 | 11/2003 |
| WO | 03103743 A2 | 12/2003 |
| WO | 2004012629 A1 | 2/2004 |
| WO | 2004030569 A2 | 4/2004 |
| WO | 2005011534 A1 | 2/2005 |
| WO | 2005034812 A1 | 4/2005 |
| WO | 2005087140 A1 | 9/2005 |
| WO | 2005102015 A2 | 11/2005 |
| WO | 2006014233 A2 | 2/2006 |
| WO | 2006034008 A2 | 3/2006 |
| WO | 2006085225 A1 | 8/2006 |
| WO | 2006108090 A2 | 10/2006 |
| WO | 2006111391 A1 | 10/2006 |
| WO | 2006138173 A2 | 12/2006 |
| WO | 2007025028 A1 | 3/2007 |
| WO | 2008005405 A2 | 1/2008 |
| WO | 2008010792 A1 | 1/2008 |
| WO | 2008035337 A2 | 3/2008 |
| WO | 2008125153 A1 | 10/2008 |
| WO | 2008147964 A1 | 12/2008 |
| WO | 2008150529 A1 | 12/2008 |
| WO | 2009024859 A2 | 2/2009 |
| WO | 2009026563 A2 | 2/2009 |
| WO | 2009042196 A2 | 4/2009 |
| WO | 2009091509 A1 | 7/2009 |
| WO | 2009094500 A1 | 7/2009 |
| WO | 2010005524 A2 | 1/2010 |
| WO | 2010008549 A1 | 1/2010 |
| WO | 2010121076 A2 | 10/2010 |
| WO | 2011002996 A2 | 1/2011 |
| WO | 2011041422 A2 | 4/2011 |
| WO | 2011081997 A1 | 7/2011 |
| WO | 2012008459 A1 | 1/2012 |
| WO | 2012032187 A1 | 3/2012 |
| WO | 2012095455 A2 | 7/2012 |
| WO | 2012099418 A2 | 7/2012 |
| WO | 2013005878 A1 | 1/2013 |
| WO | 2013028387 A2 | 2/2013 |
| WO | 2013065036 A2 | 5/2013 |
| WO | 2013106585 A1 | 7/2013 |
| WO | 2013128461 A1 | 9/2013 |
| WO | 2014009213 A1 | 1/2014 |
| WO | 2014018432 A2 | 1/2014 |
| WO | 2014079291 A1 | 5/2014 |
| WO | 2014141209 A1 | 9/2014 |
| WO | 2014145338 A1 | 9/2014 |
| WO | 2014149865 A1 | 9/2014 |
| WO | 2014163706 A1 | 10/2014 |
| WO | 2014194178 A1 | 12/2014 |
| WO | 2015004624 A1 | 1/2015 |
| WO | 2015004625 A1 | 1/2015 |
| WO | 2015057407 A1 | 4/2015 |
| WO | 2015077274 A1 | 5/2015 |
| WO | 2016002189 A1 | 1/2016 |
| WO | 2016004137 A1 | 1/2016 |
| WO | 2016016899 A1 | 2/2016 |
| WO | 2017006510 A1 | 1/2017 |
| WO | 2017035487 A1 | 3/2017 |
| WO | 2018000333 A1 | 1/2018 |
| WO | 2018213209 A1 | 11/2018 |
| WO | 2022002054 A1 | 1/2022 |
| WO | 2023006048 A1 | 2/2023 |
| WO | 2023076103 A1 | 5/2023 |
| WO | 2023081236 A1 | 5/2023 |
| WO | 2023091769 A1 | 5/2023 |
| WO | 2023096804 A1 | 6/2023 |
| WO | 2023154250 A1 | 8/2023 |
| WO | 2023196150 A1 | 10/2023 |
| WO | 2023244454 A1 | 12/2023 |
| WO | 2023244767 A1 | 12/2023 |
| WO | 2023250114 A1 | 12/2023 |
| WO | 2024001789 A1 | 1/2024 |
| WO | 2024003620 A1 | 1/2024 |
| WO | 2024007575 A1 | 1/2024 |
| WO | 2024009540 A1 | 1/2024 |
| WO | 2024010739 A1 | 1/2024 |
| WO | 2024030520 A1 | 2/2024 |

OTHER PUBLICATIONS

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
Inoue, M.D., Kanji, et al., "Clinical Application of Transvenous Mitral Commissurotomy by a New Balloon Catheter," The Journal of Thoracic and Cardiovascular Surgery 87:394-402, 1984.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Rashkind, M.D., William J., "Historical Aspects of Interventional Cardiology: Past, Present, Future," Texas Heart Institute Journal, Interventional Cardiology, pp. 363-367.
Rösch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Wheatley, M.D., David J., "Valve Prostheses," Rob & Smith's Operative Surgery, Fourth Edition, pp. 415-424, Butterworths 1986.
Bavaria, Joseph E. M.D. et al.: "Transcatheter Mitral Valve Implantation: The Future Gold Standard for MR?," Applicant requests the Examiner to consider this reference to be prior art as of Dec. 2010.

(56) References Cited

OTHER PUBLICATIONS

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.
Bavaria, Joseph E. M.D.: "CardiAQ Valve Technologies: Transcatheter Mitral Valve Implantation," Sep. 21, 2009.
Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages, Applicant believes this may have been available online as early as Feb. 7, 2011.
Boudjemline, Younes, et al., "Steps Toward the Percutaneous Replacement of Atrioventricular Valves," JACC, vol. 46, No. 2, Jul. 19, 2005:360-5.
CardiAQ Valve Technologies, "Innovations in Heart Valve Therapy," In3 San Francisco, Jun. 18, 2008, PowerPoint presentation in 19 slides.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31, Applicant believes this may have been available as early as Dec. 2006.
Feldman, Ted, MD. "Prospects for Percutaneous Valve Therapies," Circulation 2007;116:2866-2877. Applicant believes that this may be available as early as Dec. 11, 2007.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Fornell, Dave, ""Transcatheter Mitral Valve replacement Devices in Development,"" Diagnostic and Interventional Cardiology, Dec. 30, 2014, p. 3, <http://www.dicardiology.com/article/transcatheter-mitral-valve-replacement-devices-development>.
Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Karimi, Houshang, et al., "Percutaneous Valve Therapies," SIS 2007 Yearbook, Chapter 11, pp. 1-11.
Kronemyer, Bob, ""CardiAQ Valve Technologies: Percutaneous Mitral Valve Replacement,"" Start Up—Windhover Review of Emerging Medical Ventures, vol. 14, Issue No. 6, Jun. 2009, pp. 48-49.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents For Off-Pump Mitral Valve Replacement," European Journal of Cardio-thoracic Surgery 28 (2005) 194-199, Applicant believes this may have been available as early as Aug. 2005.
Mack, Michael, M.D., "Antegrade Transcatheter Mitral valve Implantation: A Short-term Experience in Swine Model," Applicant believes this may have been presented on May of 2011 at TVT.
Mack, Michael, M.D., "Antegrade Transcatheter Mitral valve Implantation: On-Going Experience in Swine Model," Applicant believes this may have been presented on Nov. 2011 at TCT.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent, "LSI EMT Spotlight," May 15, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "In3 Company Overview," Jun. 24, 2009.
Ruiz, Carlos E., "Overview of Novel Transcatheter Valve Technologies," Applicant believes this may have been presented on May 27, 2010 at EuroPCR.
Spillner, J. et al., "New Sutureless 'Atrial-Mitral-Valve Prosthesis' For Minimally Invasive Mitral Valve Therapy," Textile Research Journal, 2010, in 7 pages, Applicant believes this may have been available as early as Aug. 9, 2010.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Webb, John G., et al., "Transcatheter Aortic Valve Implantation: The Evolution Of Prostheses, Delivery Systems And Approaches," Archives of Cardiovascular Disease (2012) 105, 153-159. Applicant believes this may have been available as early as Mar. 16, 2012.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
"Company Overview," at TVT on Jun. 25, 2009.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
Neovasc corporate presentation, Oct. 2009, available at http://www.neovasc.com/investors/documents/Neovasc-Corporate-Presentation-October-2009.pdf.
AGA Medical Corporation. www.amplatzer.comproducts. "The Muscular VSD Occluder" and "The Septal Occluder" device description. Accessed Apr. 3, 2002.
Anand et al.; Isolated myocyte contractile function is normal in postinfarct remodeled rat heart with systolic dysfunction; Circulation ; 96(11); pp. 3974-3984; Dec. 1997.
Artrip et al.; Left ventricular vol. reduction surgery for heart failure: A physiologic perspective; J Thorac Cardiovasc Surg; vol. 122; No. 4; pp. 775-782; Oct. 2001.

(56) References Cited

OTHER PUBLICATIONS

Boersma et al.; Early thrombolytic treatment in acute myocardial infarction: reappraisal of the golden hour; Lancet: vol. 348(9030); pp. 771-775; Sep. 21, 1996.

Bozdag-Turan et al.; Left ventricular partitioning device in a patient with chronic heart failure: Short-term clinical follow-up; Int J Cardiol; 163(1); pp. e1-e3; (Epub) Jul. 2012.

Dang et al.; Akinetic myocardial infarcts must contain contracting myocytes: finite-element model study; Am J Physiol Heart Circ Physiol ; 288; pp. H1844-H1850; Apr. 2005.

Dang et al.; Effect of ventricular size and patch stiffness in surgical anterior ventricular restoration: a finite element model study; Ann Thorac Surg; 79; pp. 185-193; Jan. 2005.

Di Mattia et al. Surgical treatment of left ventricular post-infarction aneurysm with endoventriculoplasty: late clinical and functioal results. European Journal of Cardio-thoracic Surgery. 15(4):413-418; Apr. 1999.

Dor et al. Ventricular remodeling in coronary artery disease. Current Opinion in Cardiology. 12(6):533-537; Nov. 1997.

Dor V. The treatment of refractory ischemic ventricular tachycardia by endoventricular patch plasty reconstruction of the left ventricle. Seminars in Thoracic and Cardiovascular Surgery. 9(2): 146-155; Apr. 1997.

Dor. Surgery for left ventricular aneurysm. Current Opinion in Cardiology. vol. 5; No. 6; pp. 773-780; Dec. 1990.

Gore Medical. www.goremedical.com. "Helex Septal Occluder" product description. Accessed Apr. 3, 2002.

Grossman et al.; Wall stress and patterns of hypertrophy in the human left ventricle; J Clin Invest; 56; pp. 56-64; Jul. 1975.

Guccione et al.; Finite element stress analysis of left ventricular mechanics in the beating dog heart; J Biomech; 28; pp. 1167-1177; Oct. 1995.

Guccione et al.; Mechanics of active contraction in cardiac muscle: Part II—Cylindrical models of the systolic left ventricle; J Biomech Eng; 115; pp. 82-90; Feb. 1993.

Gutberlet et al.; Myocardial viability assessment in patients with highly impaired left ventricular function: comparison of delayed enhancement dobutamine stress MRI end-diastolic wall thickness and Tl201-SPECT with functional recovery after revascularization; Eur Radiol; 15; pp. 872-880; May 2005.

Huisman et al.; Measurement of left ventricular wall stress; Cardiovascular Research; 14; pp. 142-153; Mar. 1980.

James et al.; Blood Volume and Brain Natriuretic Peptide in Congestive Heart Failure: A Pilot Study; American Heart Journal; vol. 150; issue 5 pp. 984.e1-984.e6 (abstract); Dec. 6, 2005.

Januzzi James L.; Natriuretic peptide testing: A window into the diagnosis and prognosis of heart failure; Cleveland Clinic Journal of Medicine; vol. 73; No. 2; pp. 149-152 and 155-157; Feb. 2006.

Jones et al.; Coronary Bypass Surgery with or without Surgical Ventricular Reconstruction; N Engl J Med; 360; pp. 1705-1717; Apr. 2009.

Kawata et al. Systolic and Diastolic Function after Patch Reconstruction of Left Ventricular Aneurysms. Ann. Thorac. Surg. 5(2)9:403-407; Feb. 1995.

Lee et al.; A novel method for quantifying in-vivo regional left ventricular myocardial contractility in the border zone of a myocardial infarction (author manuscript 11 pgs.); J Biomech Eng; 133; 094506; Sep. 2011.

Mazzaferri et al.; Percutaneous left ventricular partitioning in patients with chronic heart failure and a prior anterior myocardial infarction: Results of the Percutaneous Ventricular Restoration in Chronic Heart Failure Patients Trial; Am Heart J; 163; pp. 812-820; May 2012.

Nikolic et al.; Percutaneous implantation of an intraventricular device for the treatment of heart failure: experimental results and proof of concept; J Card Fail; 15(9); pp. 790-797; Nov. 2009.

Priola et al.; Functional characteristics of the left ventricular inflow and outflow tracts; Circ Res; 17; pp. 123-129; Aug. 1965.

Sagic et al.; Percutaneous implantation of the left ventricular partitioning device for chronic heart failure: a pilot study with 1-year follow-up. Eur J Heart Fail; 12; pp. 600-606; Apr. 2010.

Sun et al.; A computationally efficient formal optimization of regional myocardial contractility in a sheep with left ventricular aneurysm (author manuscript 21 pgs.); J Biomech Eng; 131; 111001; Nov. 2009.

U.S. Food & Drug Administration; AneuRx Stent Graft System-Instructions for use; (pre-market approval); Sep. 29, 1999; downloaded Apr. 25, 2013 (http:www.accessdata.fda.govcdrh_docspdfP990020c.pdf).

Walker et al; Magnetic resonance imaging-based finite element stress analysis after linear repair of left ventricular aneurysm (author manuscript 17 pgs.); J Thorac Cardiovasc Surg; 135; pp. 1094-1102 e1-2; May 2008.

Walker et al; MRI-based finite element analysis of left ventricular aneurysm; Am J Physiol Heart Circ Physiol; 289; pp. H692-H700; Aug. 2005.

Walmsley; Anatomy of left ventricular outflow tract; British Heart Journal; 41; pp. 263-267; Mar. 1979.

Wenk et al.; First evidence of depressed contractility in the border zone of a human myocardial infarction; Ann Thorac Surg; 93; pp. 1188-1193; Apr. 2012.

Wenk et al.; Regional left ventricular myocardial contractility and stress in a finite element model of posterobasal myocardial infarction (author manuscript pgs.); J Biomech Eng; 133(4); 044501; Apr. 2011.

\* cited by examiner

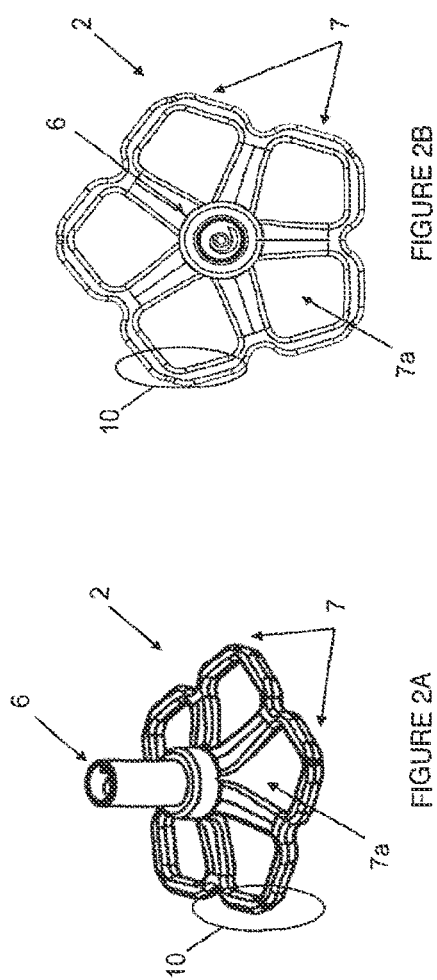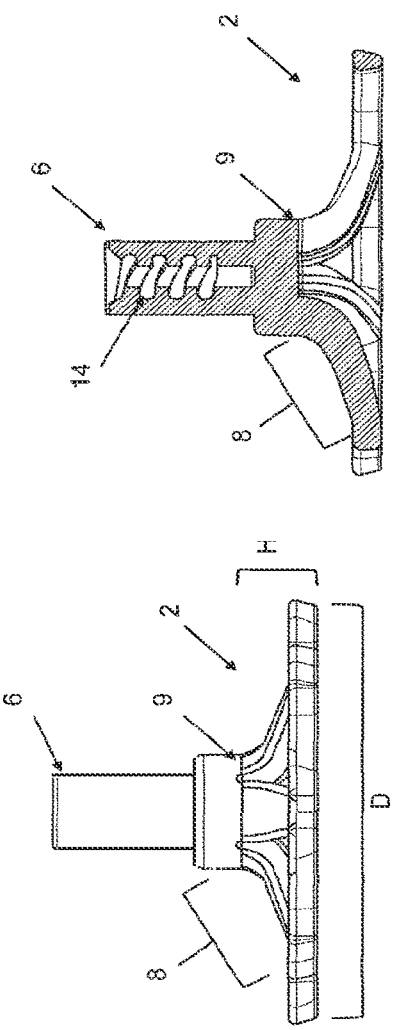

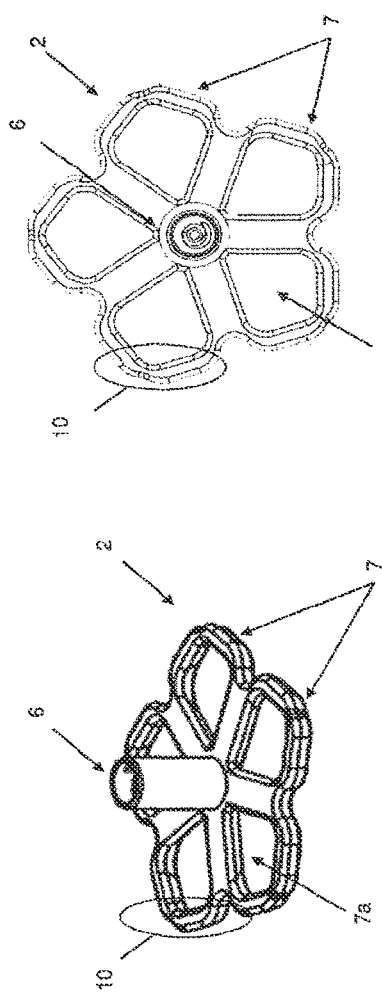
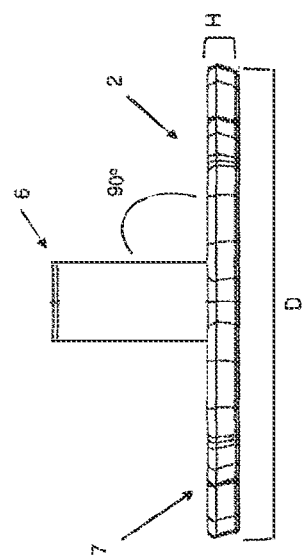

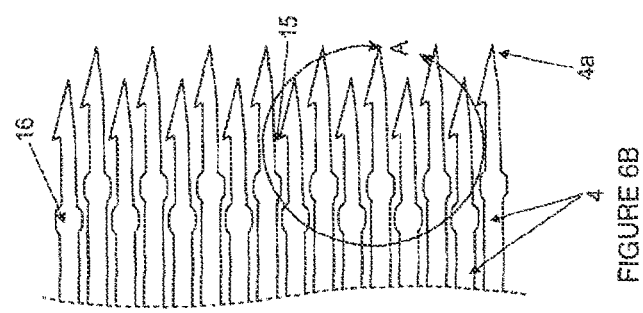
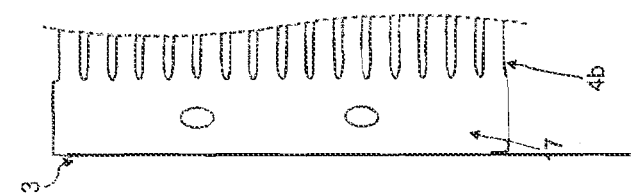
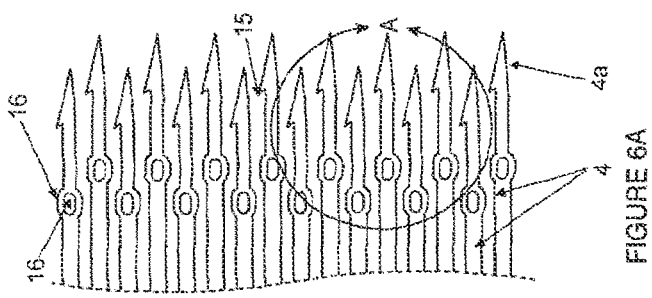
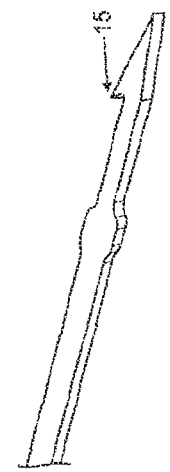

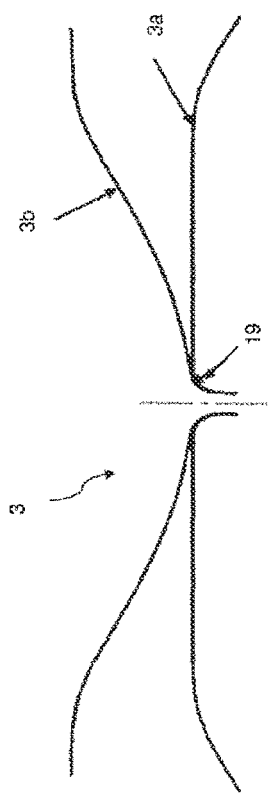
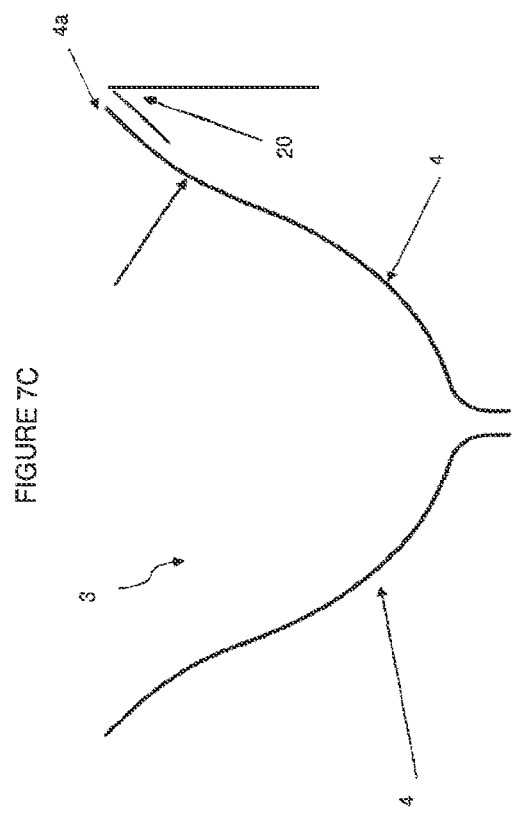
FIGURE 7C
FIGURE 7D

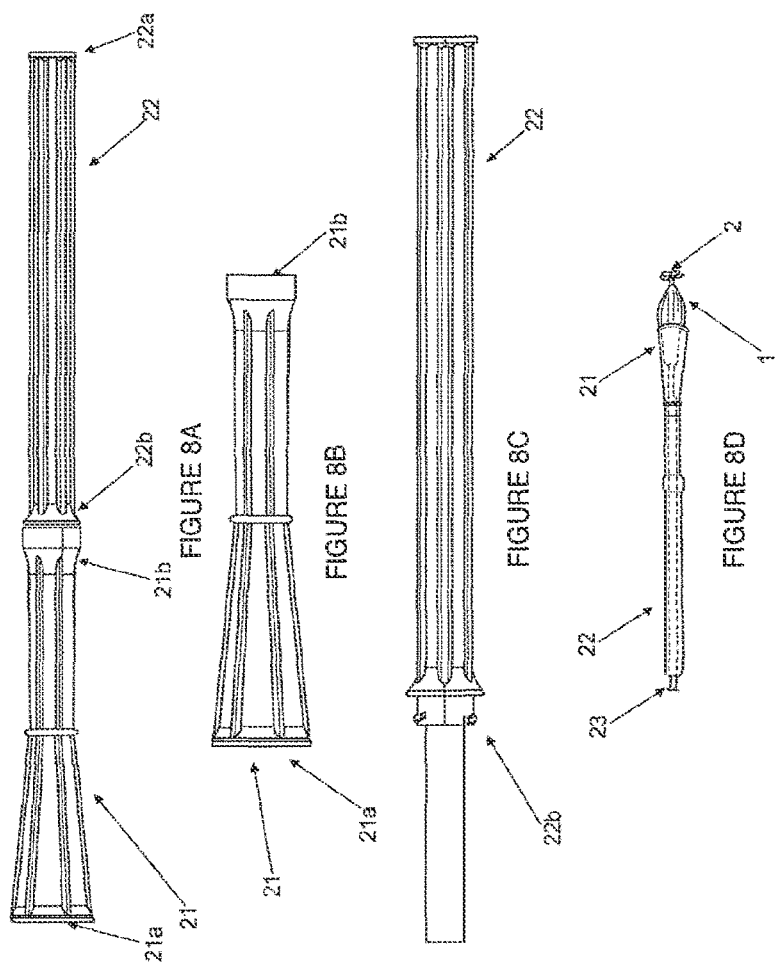

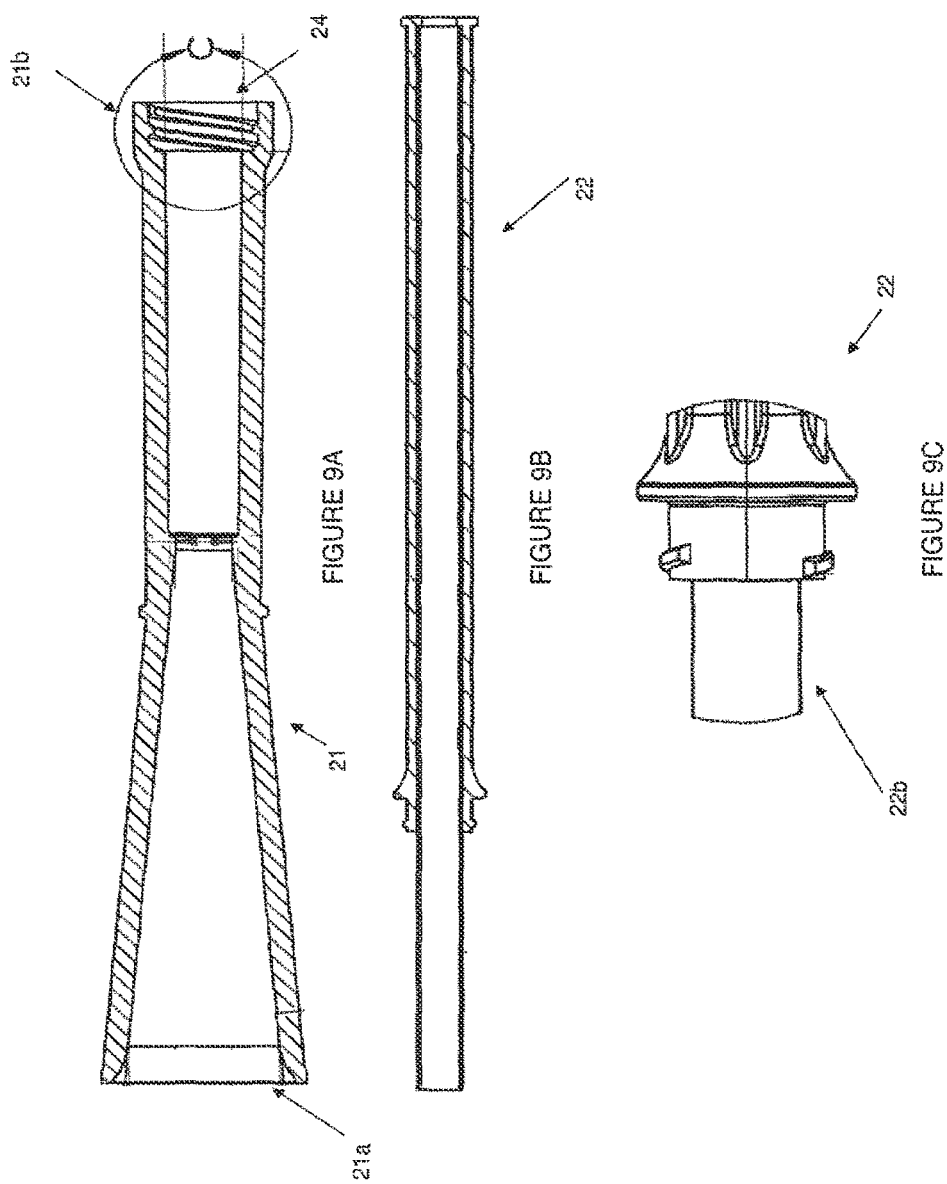

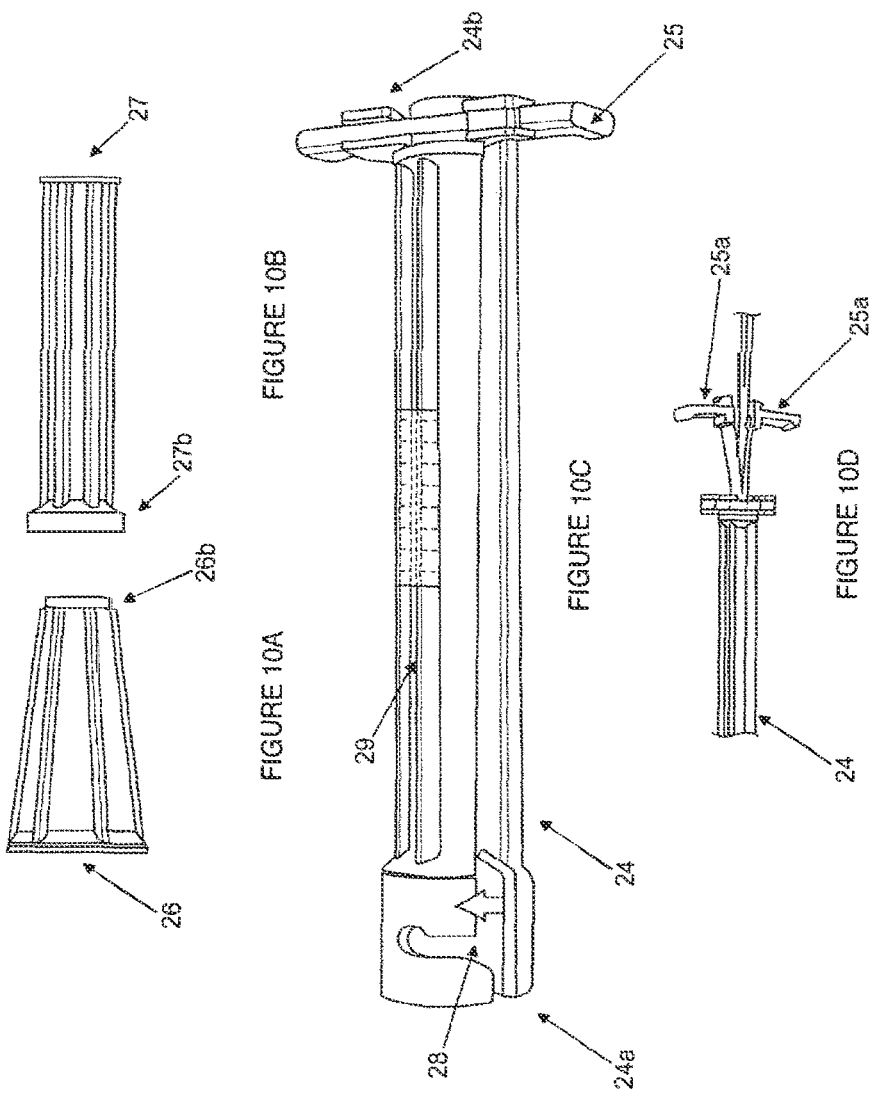

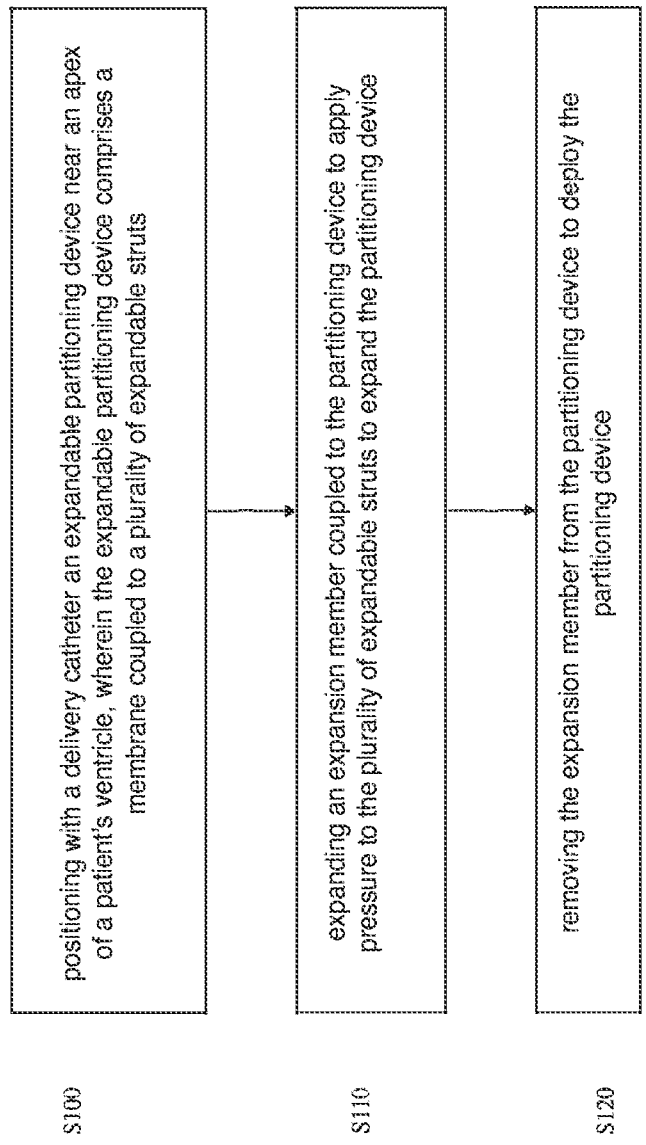

SYSTEMS AND METHODS FOR TREATING CARDIAC DYSFUNCTION

CROSS REFERENCE TO RELATED APPLICATIONS

This application is a continuation of U.S. patent application Ser. No. 16/997,634, filed Aug. 19, 2020, now U.S. Pat. No. 11,690,720, which is a continuation of U.S. patent application Ser. No. 15/506,562, filed Feb. 24, 2017, now U.S. Pat. No. 10,751,183, which claims priority to International Patent Application No. PCT/US2015/050827, filed Sep. 18, 2015, which claims priority to Chinese utility model patent application No. 201420564242.9, filed on Sep. 28, 2014 (titled "IMPLANT LOADING SYSTEMS"), which issued on Mar. 4, 2015 as ZL201420564242.9; Chinese utility model patent application No. 201420564809.2, filed on Sep. 28, 2014 (titled "EXPANDABLE DEVICES FOR INSERTING INTO A VENTRICLE OF A HEART TO TREAT HEART FAILURE"), which issued on Mar. 11, 2015 as ZL 2014205648092; and Chinese utility model patent application No. 201420564806.9, filed on Sep. 28, 2014 (titled "SYSTEMS OF EXPANDABLE DEVICES AND DELIVERY CATHETERS FOR TREATING CARDIAC DYSFUNCTION"), which issued on Feb. 25, 2015 as ZL 201420564806.9. Each of these applications is herein incorporated by reference in its entirety.

TECHNICAL FIELD

Described herein are ventricular devices useful for treating cardiac dysfunction.

BACKGROUND

Congestive heart failure (CHF) is a chronic medical condition in which the heart progressively enlarges. The enlarged heart cannot deliver sufficient oxygenated and nutrient rich blood to the body's cells. CHF is commonly associated with left ventricular dysfunction and/or diastolic dysfunction. Left ventricular dysfunction results from impaired emptying of the left ventricular heart chamber. In contrast, diastolic dysfunction refers to alterations in left ventricular properties that adversely affect ventricular filling and diastolic pressure.

A key aspect of normal diastolic filling is the contribution of left ventricular elastic recoil forces to left ventricular filling. Elastic recoil is the ability of the stretched heart to return to its resting position. For example, in a healthy heart, the end-diastolic dimension of the left ventricle may range from 36-56 mm (relaxed) and the end-systolic dimension of the left ventricle may range from 20-40 mm (contracted). A left ventricle in heart failure would typically have larger dimensions than those of a healthy heart. Elastic recoil forces are important in early diastole because they allow rapid and enhanced early filling by assisting the expansion of the left ventricle.

In the case of heart enlargement and/or a decrease in myocardial function, elastic recoil forces may be reduced or absent, thus ceasing to assist early ventricular filling and leading to an increase of the ventricular filling pressure. For example, a patient experiencing CHF typically has an ejection fraction of 40% or less.

Thus, there is a need for a new and useful system, device, and method for treating cardiac dysfunction. This new and useful apparatuses (e.g., systems, devices, and assemblies) and methods described herein may address these needs.

SUMMARY

Described herein are devices and systems for treating a cardiac dysfunction. In general, the devices and systems described herein may include improved expandable implant devices that can be collapsed for insertion into a ventricle of a human heart, and then expanded when in the heart. In general, the implants described herein are improved over earlier generations of implants because they may be used more safely and reliably. In particular, such devices may include a support frame having a plurality of expandable struts, to which a membrane is attached, where the struts are configured for cyclical loading. The struts of the support frame may have a roughness average of less than 1 μm. These expandable implants may also include a foot configured for contacting a first interior wall portion of the ventricle, wherein the first free ends of the struts extend beyond a diameter of the foot. The foot may have a durometer of between about 70 A to 90 A.

For example, an expandable device for inserting into a ventricle of a heart to treat heart failure may be characterized in that the device has: a support frame comprising a plurality of radially expandable struts, wherein each strut has a first free end and a second end, and wherein the struts are configured for cyclical loading; a foot configured for contacting a first interior wall portion of the ventricle, wherein the first free ends of the struts extend beyond a diameter of the foot; and a membrane coupled to the support frame.

Each of the first ends of the plurality of struts may comprise an anchor for engaging a second interior wall portion of a heart. The anchors may be staggered. Each strut may include a stop proximate the anchor, the stop may be adapted to keep the membrane in place on the support frame while also being adapted to reduce or prevent over-penetration of the strut into the second interior wall portion of the heart. The stop may include an eyelet.

The struts are adapted for cyclic loading. Cyclic loading means that the struts are configured to move (e.g. flex or bend) as the heart, and particularly the ventricle, beats. In addition, the membrane attached to the struts may push against blood flowing in the ventricle, and assist in ejecting blood from the ventricle. Repeated cyclic loading may weaken struts over time, which is particularly critical when the device is implanted into a heart. Thus, the struts described herein may be shaped with a curve and/or varying thickness, particularly in regions prone to stress fractures. For example, the struts may have a thickness that varies along the length of the struts. This is illustrated in greater detail below.

The support frame generally has a collapsed delivery configuration and an expanded deployed configuration.

The second ends of the plurality of struts may be flared, such that the width of the second ends is greater than the width of the first ends. A slot region may be disposed between two struts (e.g., between adjacent struts).

The support frame may have a roughness average of less than 1 μm.

In general, the foot may comprise a radiopaque material. The foot may be compressible or bendable. The foot may have a durometer between about 70 A to 90 A. The foot may have a height between about 0.5 mm to 4.0 mm.

For example, an expandable device for inserting into a ventricle of a heart to treat heart failure may be characterized in that the device has: a foot configured for contacting a first interior wall portion of a heart, wherein the foot has a durometer between about 70 A to 90 A; a support frame comprising a plurality of radially expandable struts configured for cyclical loading, wherein each strut has a first free end and a second end configured to extend beyond the foot; and a membrane coupled to the support frame, wherein each strut includes a stop proximate the free end, the stop adapted to keep the membrane in place on the support frame while also being adapted to reduce or prevent over-penetration of the strut into the second interior wall portion of the heart.

Also described herein are systems including both an expandable device, including any of the improved expandable devices described above, and a delivery catheter.

For example, a system including an expandable device for inserting into a heart ventricle to treat heart failure and a delivery catheter for deploying the expandable device into the ventricle may be characterized (improved from other such systems) in that the system includes: the expandable device comprising: a foot for contacting a first interior wall portion of a heart; a support frame comprising a plurality of radially expandable struts, wherein each strut has a first free end and a second end coupled to the foot; and a membrane coupled to the support frame; and the delivery catheter having: a proximal end and a distal end; an expansion member near the distal end of the delivery catheter configured to apply pressure to the support frame of the ventricular partitioning device to move the ventricular partitioning device from a collapsed delivery configuration to an expanded deployed configuration; and a coupling element configured to secure the expansion member to the ventricular partitioning device during deployment.

In general the expandable device (which may also be referred to as a ventricular partitioning device herein) may be configured to be loaded into a guide catheter using a funnel coupleable to a sleeve, as described in greater detail below. The system first ends of the plurality of struts may comprise an anchor for engaging a second interior wall portion of a heart. The anchors on the first ends of the plurality of struts may be configured to penetrate the second interior wall portion of the heart upon expanding the ventricular partitioning device. The coupling element may comprise a helical screw.

As mentioned above, the support frame may have a roughness average of less than 1 µm, and the foot may have a durometer between about 70 A to 90 A.

Any of these systems may also include a funnel with a flared first end and a second end, wherein the flared first end is configured for receiving the expandable device. Any of the funnels may include a sleeve removably coupled to the second end of the funnel, wherein the sleeve is configured to transfer the expandable device to a guide catheter.

For example, a system may include including an expandable device for inserting into a heart ventricle to treat heart failure and a delivery catheter for deploying the expandable device into the ventricle, characterized in that the system comprises: the expandable device having: a foot for contacting a first interior wall portion of a heart having a durometer between about 70 A to 90 A; a support frame having a roughness average of less than 1 µm, the support frame comprising a plurality of radially expandable struts, wherein each strut has a first free end and a second end coupled to the foot; and a membrane coupled to the support frame; the delivery catheter having: a proximal end and a distal end; an expansion member near the distal end of the delivery catheter configured to apply pressure to the support frame of the expandable device to move the expandable device from a collapsed delivery configuration to an expanded deployed configuration; and a coupling element configured to secure the expansion member to the expandable device during deployment.

Also described herein are systems or devices for loading the implant (expandable devices) described above. These device or systems may include a funnel and a releasably coupled sleeve. An implant may be coupled with the funnel and sleeve, for transferring to a delivery catheter.

For example, described herein are implant loading systems including a funnel for loading an expandable implant into a guide catheter for delivery to a ventricle to treat heart failure, characterized in that the implant loading system comprises: the funnel having: a flared first end and a second end, wherein the flared first end is configured for receiving and collapsing expandable implant; and a sleeve removably coupled to the second end of the funnel, wherein the sleeve is configured to transfer the expandable implant to a guide catheter.

The funnel may include a first portion at the first end and a second portion at the second end, the first portion comprising a tapering receptacle for receiving the expandable implant, and the second portion comprising a lumen having a first diameter.

The sleeve may include a lumen with a second diameter, wherein the first diameter is greater than the second diameter. The sleeve may also include a coupling element located in a center portion of the sleeve.

The sleeve may comprise a tubular portion distal to the coupling element, the tubular portion may be configured to be inserted into the second portion of the funnel. The tubular portion of the sleeve may have a length that is about equal to the length of the lumen of the second portion of the funnel.

In general, any of the implants described herein may be used with the implant loading devices and systems. For example, an expandable implant that may be used (or included with) these systems and devices may comprise: a foot; a support frame comprising a plurality of radially expandable struts, wherein each strut has a first free end and a second end coupled to the foot; and a membrane coupled to the support frame.

The flared first end of the funnel may be configured for receiving the first free end of the plurality of radially expandable struts. The implant loading system may be coupled to the expandable implant.

For example, an implant loading system including a funnel for loading an expandable implant into a guide catheter for delivery to a ventricle to treat heart failure, characterized in that the implant loading system comprises: the funnel having: a flared first end and a second end, wherein the flared first end comprises a tapering receptacle for receiving and collapsing the expandable implant, and a second portion at the second end comprising a lumen having a first diameter; and a sleeve removably coupled to the second end of the funnel, wherein the sleeve is configured to transfer the expandable implant to a guide catheter; a coupling element located in a center portion of the sleeve; and a tubular portion distal to the coupling element, the tubular portion configured to be inserted into the second portion of the funnel.

BRIEF DESCRIPTION OF THE DRAWINGS

FIGS. 2A-2D illustrate a foot of a ventricular partitioning device in accordance with a preferred embodiment;

FIGS. 3A-3C illustrate a foot of a ventricular partitioning device in accordance with an alternative preferred embodiment;

FIGS. 6A-6C illustrate two embodiments of the struts of a ventricular partitioning device;

FIGS. 7A-7D illustrate a support frame, in accordance with a preferred embodiment;

FIGS. 8A-8D illustrate an exterior view of an implant loading system for a ventricular partitioning device, in accordance with a preferred embodiment;

FIGS. 9A-9C illustrate a cross-sectional view of an implant loading system for a ventricular partitioning device, in accordance with a preferred embodiment;

FIGS. 10A-10D illustrates an implant loading system for a ventricular partitioning device, in accordance with an alternative preferred embodiment;

FIG. 12 describes a method of using a delivery system for a ventricular partitioning device, in accordance with a preferred embodiment.

DETAILED DESCRIPTION

Disclosed herein are systems and devices for treating cardiac dysfunction. In some instances, cardiac dysfunction may include diastolic dysfunction, mitral valve regurgitation, and/or heart failure.

In general, the systems and devices described herein may be used to treat a patient's heart suffering from heart failure. The systems and devices may be used to treat a patient's heart experiencing diastolic dysfunction or a condition exhibiting characteristics of diastolic dysfunction, and may involve implanting within a ventricle of the heart a device that partitions the ventricle into functional and nonfunctional portions. In some embodiments, the device may deform during systole and recoil during diastole to supplement the natural elastic recoil action of the ventricle. In some embodiments, the device may reduce the end-diastolic volume, end-diastolic pressure, and/or increase the ejection fraction.

Diastole represents the period of time in the heart cycle in which the ventricles are relaxed and not contracting. Throughout most of diastole, blood is passively flowing from the right and left atria into the right and left ventricles, respectively. As the ventricles begin to contract, the pressure in the ventricles exceeds that of the atria, and the mitral valve closes, ending diastole. At this time, the ventricular pressure and volume are referred to as end-diastolic pressure and end-diastolic volume, respectively.

Reduced ventricular compliance, for example due to an increased stiffness in the ventricular heart wall, may result in increased end-diastolic pressure and decreased end-diastolic volume. Diastolic dysfunction may also result from changes in left ventricle relaxation during diastole. For example, inotropic stimulation, fast heart rates, non-uniform heart activation, and altered timing of forces that oppose ventricular ejection may contribute to altered left ventricle relaxation.

Devices

Figure 1:
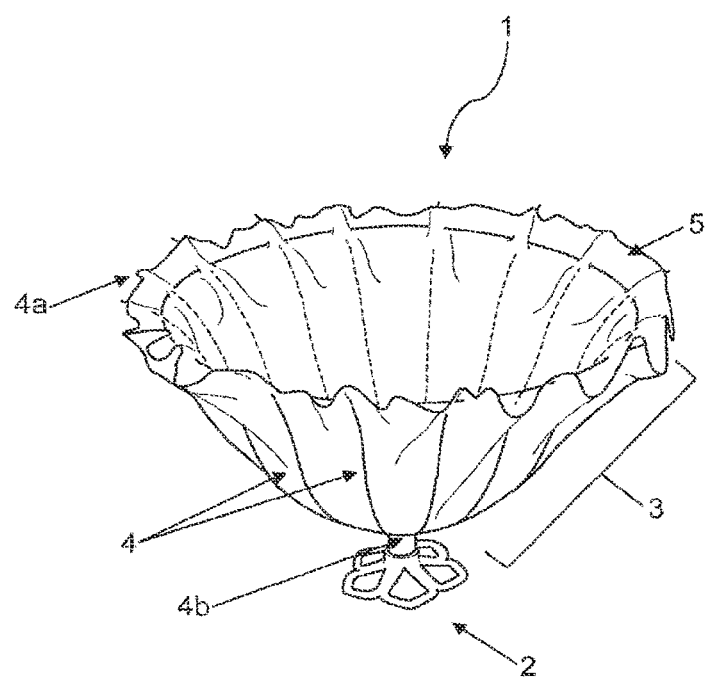
FIG. 1 illustrates a ventricular partitioning device in accordance with a preferred embodiment.

FIG. 1 illustrates an expandable device, which may also be referred to as a ventricular partitioning device, 1 to treat cardiac dysfunction. In some embodiments, cardiac dysfunction may include diastolic dysfunction, mitral valve regurgitation, heart failure, and/or any other type of malady of the heart. The device may be delivered to the ventricle of a patient to treat cardiac dysfunction. In some embodiments, as shown in FIG. 1, a device for treating cardiac dysfunction may include a foot 2 for contacting a first interior wall portion of a heart. Further, in some embodiments, a device for treating cardiac dysfunction may include a support frame 3 including a plurality of radially expandable struts 4 and a membrane 5 coupled to the support frame 3. Each of the radially expandable struts 4 has a first free end 4a and a second end 4b coupled to the foot 2.

FIGS. 2A-2D and 3A-3C illustrate a foot 2 coupled to a stem 6 of an expandable device in accordance with a preferred embodiment and an alternative preferred embodiment, respectively. The foot 2 of a ventricular partitioning device may contact an interior wall portion of a heart of a patient experiencing cardiac dysfunction. An interior wall portion of a heart may include an apex of a ventricle. In some embodiments, the foot 2 may contact the apex of the ventricle so that the entire device is underneath the papillary muscle located in the ventricle, such that the ventricular partitioning device does not interfere with the heart valve in the apex of the ventricle. In some embodiments, the foot 2 may contact the apex of the ventricle atraumatically such that the apex of the ventricle does not incur damage, trauma, and/or significant injury.

The foot 2 of the device, as shown in FIGS. 2A-3C, is supportive such that it does not collapse upon itself once implanted. However, the foot 2 may also be flexible, such that the device does not create focal pressure points (e.g., "hot spots") in the ventricle. To balance these properties of the ventricular partitioning device, the foot 2 of the ventricular partitioning device may include a thermoplastic elastomer. In some embodiments, the foot 2 may include thermoplastic silicone polyether polyurethane (TPU), such as DSM.

In some embodiments, as shown in FIGS. 2A-3C, the foot 2 may include a different material and/or durometer than the stem. In some embodiments, the foot 2 may include, Pursil TSPU, or any other thermoplastic material, such that the durometer is 70 A to 90 A, preferably 78 A to 84 A, and the flexural modulus or bending modulus is 15 MPa to 45 MPa, preferably 20 MPa to 40 MPa. In some embodiments, the stem 6 may include, elasthane TPU, or any other thermoplastic material, such that the durometer is 45 D to 75 D, preferably 50 D to 70 D, and the flexural modulus or bending modulus is 100 MPa to 400 MPa, preferably 145 MPa to 390 MPa.

In some embodiments, the foot 2 of the ventricular partitioning device may include a radiopaque filler material to aid in visualization of the implant during and/or after implantation of the ventricular partitioning device in the heart of a patient. In some embodiments, the foot 2 may include 20% radiopaque filler. Alternatively, the foot 2 and stem 6 may include 40% radiopaque filler and any other percent of radiopaque filler suitable to the application. For example, the foot 2 and/or stem 6 may include between about 10 and 50% radiopaque filler, or at least about 10, 20, 30, or 40% radioapaque filler.

In some embodiments, as shown in FIGS. 2C and 3C, the foot 2 may have a height H ranging from 0.5 mm to 4.0 mm and a diameter D ranging from 13 mm to 17 mm, depending on the distance between the apex of the ventricle and the papillary muscle in the ventricle. In some embodiments, the foot 2 of the ventricular partitioning device may comprise a plurality of sections or petals 7. In some embodiments, a foot 2 may include 1, 2, 3, 4, 5, 6, 7, 8, 9, or 10 petals, preferably 5 petals, as shown in FIGS. 2A, 2B, 3A, and 3C. The petals 7 may include a looped configuration such that each petal includes an aperture 7a. Alternatively, the petals may comprise a solid configuration. Each petal 7 may be coupled to at least two other petals 7 of the foot 2 of the ventricular partitioning device. Alternatively, each petal 7 of the foot 2 may be separate and uncoupled from the other petals 7 of the foot 2. In some embodiments, the foot may alternatively include a screw for securing the ventricular partitioning device to the apex, a hub, or any other component suitable for positioning a ventricular partitioning device in a heart.

In some embodiments, as shown in FIGS. 2A, 2C, and 2D, the petals 7 of the foot 2 may be curved or include an angled portion 8, such that the point of attachment 9 of the petals 7 to the stem 6 is held at a distance from the apex of the ventricle while the perimeter 10 of the petals 7 is contacting the apex of the ventricle, as shown in FIGS. 2A and 2B. Alternatively, as shown in FIGS. 3A and 3C, the petals 7 may be coupled to the stem 6 at a right angle (90°) to the stem 6, such that the entire perimeter 10 and/or surface area of the petals 7 of the foot 2 may contact the apex of the ventricle.

In some embodiments, as shown in FIGS. 3A-3C, the foot 2 may be used in a ventricular partitioning device for treating acute myocardial infarction in order to prevent cardiac remodeling or damage (configured as an endocardial implant). In this embodiment, the device is configured to be positioned immediately adjacent to the heart wall, for example similar to a patch, across from the region of the infarct.

Figure 4A:
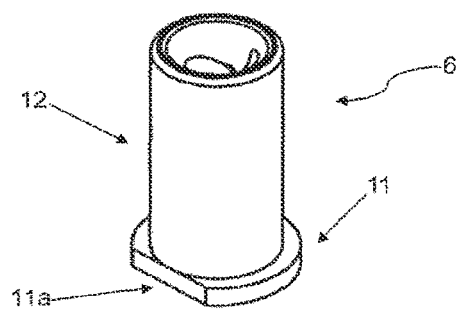
FIGS. 4A-4C illustrate a stem for coupling a membrane to a foot of a ventricular partitioning device, in accordance with a preferred embodiment.
Figure 4B:
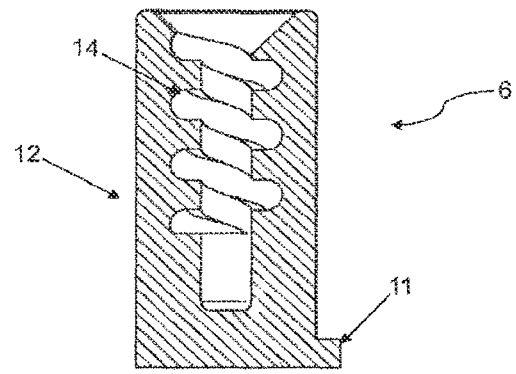
Figure 4C:
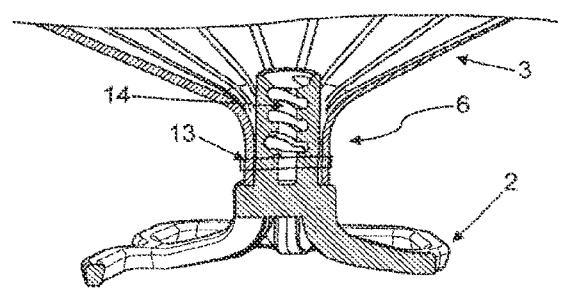

FIGS. 2A-3C illustrate a stem 6 coupled to a foot 2 of a ventricular partitioning device, such that the stem 6 is configured to receive a support frame of a ventricular partitioning device, as shown in FIG. 1. In some embodiments, the stem 6 may be substantially rigid for coupling to the support frame. However, the stem 6 may also be flexible for increasing the elastic recoil force of the ventricular partitioning device. The stem 6, as shown in FIGS. 4A-4C, may include a base 11 and a shaft 12 for receiving a support frame. In some embodiments, as shown in FIG. 4A, the base 11 may include a flange 11a to create a strong bond between the stem 6 and the foot 2 of the ventricular partitioning device. For example, the petals of the foot may be injection molded around the base of the stem and flange. Alternatively, in some embodiments, the stem 6 may be coupled to the foot 2 by another mechanism, for example by screwing, soldering, sintering, snapping, locking, fastening, or any other type of reversible or irreversible coupling mechanism.

FIGS. 4B-4C illustrate a cross-section of a stem 6 of a ventricular partitioning device in accordance with a preferred embodiment. The stem 6 may serve as an interface between the foot 2 and the support frame 3 of the ventricular partitioning device. As shown in FIG. 4C, the foot 2 may be secured to the support frame 3 by a cross pin 13 or any other type of fastener. For example, the hub or shaft at the base of the support frame may slide over the shaft 12 of the stem 6, such that a pin 13 may be inserted through the cross-section of the stem 6 to couple the support frame 3 to the stem 6. Alternatively, the support frame may be soldered, fastened, glued, or otherwise reversibly or irreversibly coupled to the stem. In some embodiments, the shaft 12 of the stem 6 may be configured to receive a delivery catheter, as described below in association with FIG. 10. For example, the shaft 12 may include helical grooves 14 such that a shaft of the delivery catheter may be screwed into the shaft of the stem 6, as shown in FIGS. 2D, 4B, and 4C.

Figure 5A:
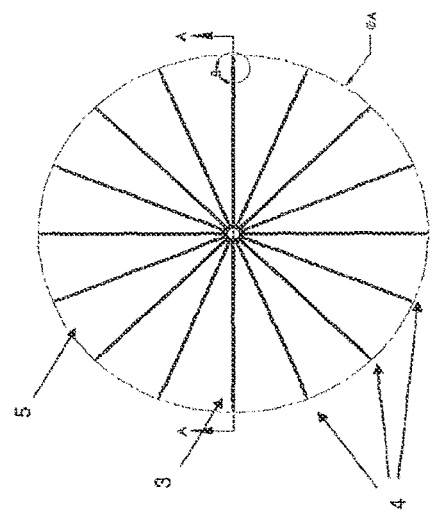
FIGS. 5A and 5B illustrate a top and side view of a membrane coupled to a support frame of a ventricular partitioning device, respectively, in accordance with a preferred embodiment.
Figure 5B:
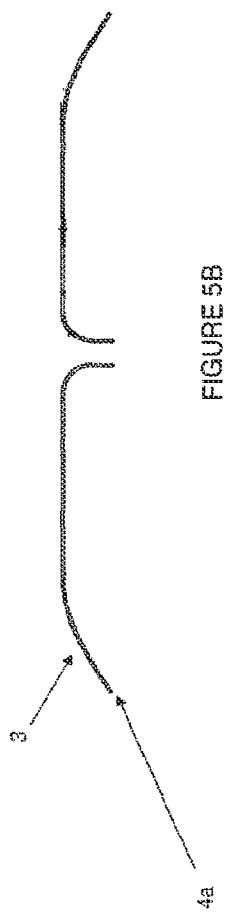

FIGS. 5A and 5B illustrate a top view and side view, respectively, of a membrane 5 coupled to a support frame 3 of a ventricular partitioning device in accordance with a preferred embodiment. The membrane 5 coupled to the support frame 3 is a pressure-receiving surface of the ventricular partitioning device, such that the elastic recoil force of the ventricle is improved when the ventricular partitioning device is implanted. The membrane 5 may be stretched over the struts to give the frame a disk like shape. The membrane 5 may include expanded Polytetrafuoroethylene (ePTFE) having a thickness between 0.01 mm and 1 mm, preferably about 0.08 mm. Alternatively, in some embodiments, the membrane 5 may include mesh, or other appropriate permeable, semi-permiable, or impermeable membranes. In some embodiments, the membrane 5 may be formed of a suitable biocompatible polymeric material including Nylon, PET (polyethylene terephthalate) and polyesters such as Hytrel. In some embodiments, the membrane 5 may be porous to facilitate tissue ingrowth after deployment within a patient's heart.

As shown in FIG. 5B, the first free ends 4a of the support frame 3 coupled to the membrane 5 may deflect away from the centerline axis of the ventricular partitioning device when the ventricular partitioning device is deployed in a ventricle. The deflection may improve the anchoring of the ventricular partitioning device to an interior wall of a ventricle.

In some embodiments, as shown in FIGS. 5A, 6A, and 6B, the support frame 3 may include a plurality of radially expandable struts 4. The struts 4 may be configured to support a membrane 5 coupled to the struts. The struts 4 may improve the elastic recoil properties of the membrane 5 coupled to the struts 4. In some embodiments, the struts 4 may be configured for anchoring the ventricular partitioning device to an interior wall of the ventricle. In some embodiments, the support frame 3 may include 5 struts, 10 struts, 15 struts, or 20 struts, preferably 16 struts. In some embodiments, each strut 4 may be 1 to 8 cm in length, preferably 3 to 6 cm. In some embodiments, the support frame 3 may be smoothed to a particular surface roughness to reduce trauma to the patient during delivery and improve characteristics of the ventricular partitioning device, such as corrosion resistance and durability. The support frame 3 may be electropolished, chemically treated, and/or mechanically polished by a wheel, tumbling, abrasion, sand blasting, chemical etching, and/or any other method of polishing to achieve a particular surface roughness. In some embodiments, the roughness average (Ra) of the support frame may be between 0.01 μm and 1 μm, preferably between 0.85 μm and 0.15 μm.

In some embodiments, as shown in FIGS. 6A-6C, each strut 4 of the support frame 3 may include a first free 4a end and a second end 4b coupled to the foot. The first free end 4a of the support frame 3 may include an anchor or barb 15 for coupling the support frame 3 to an interior wall portion of a heart. This anchoring may allow the ventricular partitioning device to contract and relax with each systolic and diastolic phase, respectively, of the heart cycle. Further, the anchoring may partition the heart into functional and non-functional portions, such that the non-functional portion is proximal to the foot of the ventricular partitioning device.

In some embodiments, as shown in FIGS. 6A-6C, a stop 16 may be located at or near the base of the anchors 15 proximal to the first free end 4a of the struts 4. The stop 16 may be a bulge, projection, or otherwise widening of a portion of the strut 4 near the first free end 4a, which serves to lock the support frame 3 in place and/or reduce or prevent over-penetration of the struts 4 into the ventricle wall. The length of the struts 4 may alternate between a short length strut and a long length strut so that the anchors 15 and/or stops 16 are staggered, which allows the struts 4 to be collapsed into a more compact diameter for delivery.

In some embodiments, as shown in FIG. 6A, each first free end 4a of the strut 4 of the support frame 3 may further include an eyelet 16a. The eyelet 16a may serve as a stop 16, as described above, and/or as a mechanism to couple the membrane to the support frame. During manufacturing, polymer may be melted near the eyelet 16a of the support frame 3 to couple the membrane to the support frame, such that the melted polymer may flow from one side of the strut 4 through the eyelet 16 to the other side of the strut 4 to couple the membrane to the struts 4. As shown in an alternative embodiment in FIGS. 6B-6C, the stop 16, as described above, may be manufactured without an eyelet, such that the polymer melts around the stop 16 and secures the membrane to the support frame 3.

Figure 7B:
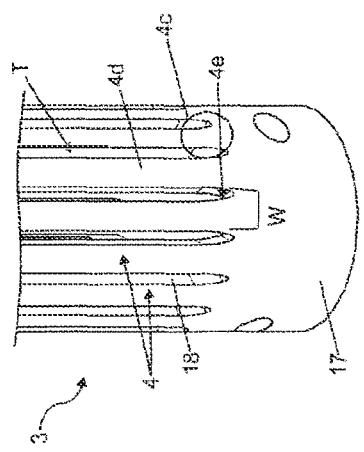
Figure 7A:
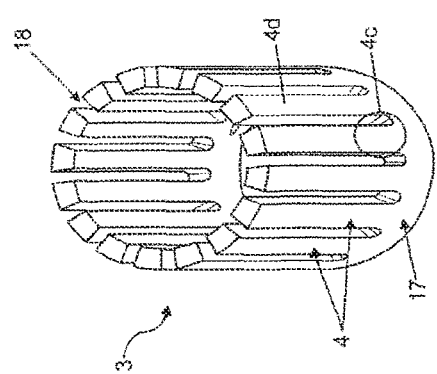

In some embodiments, as shown in FIGS. 7A-7D, the struts may include a material such as, for example, Nitinol, stainless steel, titanium alloys, NiTi alloy, other metal alloys, or plastic composites. In some embodiments, the struts 4 and/or support frame 3 may include a material, which allows for compression of the first free ends towards the central axis during delivery and self expansion upon deployment of the ventricular partitioning device in a patient's heart. In some embodiments, the struts 4 and/or support frame 3 may be cut, for example by a laser, from a tube including Nitinol, stainless steel or a similar material. During manufacturing, a plurality of longitudinal cuts may extend from one end of the metal tube to a position offset from the other end of the tube, leaving a hub 17 from which the struts 4 extend. The cuts may result in a plurality of slots 18 between the struts 4. In some embodiments, as shown in FIG. 7A, the spacing between the slots 18 may define the strut width W while the thickness of the tube may define the strut thickness T. In some embodiments, the spacing of the slots 18 around the tube may result in struts 4 having a cross-sectional width that is slightly greater than its cross-sectional thickness. This may be accomplished by the slot 18 having a slightly greater spacing than the thickness of the tube. In some embodiments, slightly greater may mean about 1, 2, 3, 4, 5, 10, 15, 20, or 25 percent, or may mean between about 1 to 25 percent, or may mean between about 5 to 20 percent.

In some embodiments, as shown in FIG. 7B, the base 4c of the strut 4 is the second end of the strut that couples to the foot and extends from the hub 17. The base 4c of the strut 4 may be flared such that the width of the strut 4 increases as it approaches the hub 17. In some embodiments, the flared base 4c may spread bending strains over a larger amount of material, thereby decreasing peak strains during manufacturing, loading of the implant within a catheter, and cyclical use in the ventricle after implantation. In some embodiments, the width of the strut 4 at the hub 17 may be about 5 to 25 percent larger than the width of the strut 4 at a middle portion of the strut 4. In some embodiments, the length of the flared base 4c may be about equal to the width of the flared base 4c at the hub 17. Alternatively, the length of the flared base 4c may be greater than about 5, 10, 15, 20, 25, 30, 35, 40, 45, 50, 75, 100, or 200 percent of the width of the flared base 4c at the hub 17. Alternatively, the length of the flared base 4c may be less than about 95, 90, 85, 80, 75, 70, 65, 60, 55, or 50 percent of the width of the flared base 4c at the hub 17. The flared base may be formed by tapering the slot as it reaches the hub.

As illustrated in FIG. 7C, in some embodiments, the flared base can have a base bend radius 19 that is sized to (1) reduce or limit peak strains during shape setting to reduce or prevent damage and cracking of the metal frame; (2) reduce or limit peak strains when the implant is loaded into the catheter and reduce or prevent plastic deformation of the metal; and (3) reduce or minimize the height of the implant. In some embodiments, the diameter of the support frame 3 in its free shape 3a can be slightly oversized relative to its laminated shape 3b so that the membrane will stay tight after lamination. For example, the support frame 3 can be oversized by about 3, 4, 5, 6, or 7 mm, or be oversized between about 2 to 10 mm. The lamination mold is designed to conform to the natural shape of the support frame 3 when it is reduced to the lamination diameter 3b. This ensures that the support frame 3 is free to move as designed with little or no alternating strain concentrations.

As shown in FIG. 7D, after lamination, there is a strut curvature 20 near the anchor on the free ends 4a of the struts 4 that is designed to optimize the angle of engagement with the left ventricle wall which improves retention of the implant in the left ventricle. In some embodiments, the strut curvature 20 has a radius of about 0.5 to 1.5 inches. In some embodiments, the angle of engagement is about 30 to 60 degrees.

In some embodiments as described above, the strut cross-section dimensions having a width slightly greater than the thickness, in conjunction with the flared base, may bias the strut so that it deflects outwardly without any significant twist. This may improve the strength of the struts and reduce strain.

System

Figure 11:
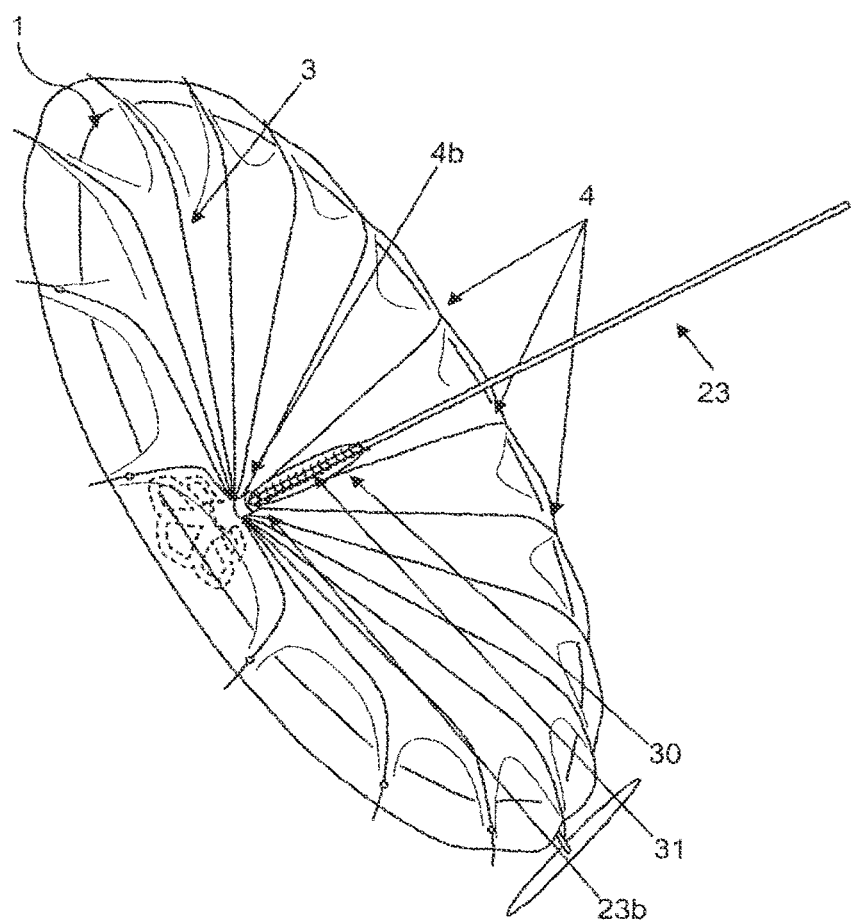
FIG. 11 illustrates a delivery catheter for a ventricular partitioning device, in accordance with a preferred embodiment.

In some embodiments, a delivery system for a ventricular partitioning device may include an implant loading system for collapsing the ventricular partitioning device into a substantially linear delivery configuration for passage into a delivery catheter and into a heart and expanding the ventricular partitioning device into an umbrella-like shape once the device is delivered into a heart. In some embodiments, the ventricular partitioning device may be delivered transapically, percutaneously, endovascularly, or through any other appropriate means or procedure. In some embodiments, the ventricular partitioning device is coupled to a shaft in a lumen of the delivery catheter, for example by screwing the ventricular partitioning device to a shaft in a lumen of the delivery catheter, as shown in FIG. 11.

Described below are two different embodiments of an implant loading system for loading a ventricular partitioning device into a delivery catheter. The system described in FIGS. 8A-9C is the preferred embodiment of the implant loading system. The system as shown in FIGS. 8A-9C requires fewer steps and components as compared to the implant loading system described in FIGS. 10A-10D. However, as evident to one of skill in the art, both implant loading systems may be used to load a ventricular partitioning device into a lumen of a delivery catheter for delivery to a heart of a patient.

In some embodiments, as shown in FIGS. 8A-9C, an implant loading system for a ventricular partitioning device may include a funnel 21 with a flared first end 21a and a second end 21b, wherein the flared first end 21a is configured for receiving a collapsed ventricular partitioning device 1, as shown in FIGS. 8B and 8D, and a sleeve 22 removably coupled to the second end 21b of the funnel 21, such that the sleeve 22 is configured to transfer the ventricular partitioning device 1 to a guide catheter, as shown in FIGS. 8C and 8D.

FIGS. 8A-8D and 9A-9C illustrate an exterior and cross-sectional view, respectively, of an implant loading system for a ventricular partitioning device, in accordance with a preferred embodiment. As shown in FIGS. 8A-8D, a ventricular partitioning device 1 may be coupled to a delivery catheter, 23, as described below. The ventricular partitioning device 1 may be collapsed by drawing at least two sutures, strings, ties, or threads together, such that the diameter of the membrane and thus the ventricular partitioning device is reduced, and the ventricular partitioning device 1 is at least partially collapsed around the delivery catheter 23. In some embodiments, the at least two sutures may be coupled by a tab, such that both sutures may be tensioned and the ventricular partitioning device at least partially collapsed by manipulating the tab. In some embodiments, the ventricular partitioning device may be positioned in the flared first end 21a of the funnel 21 with the first free ends of the struts of the ventricular partitioning device entering the flared first end 21a of the funnel 21 followed by the foot 2 of the ventricular partitioning device, as shown in FIG. 8D. The funnel 21 may function to fully collapse the ventricular partitioning device for advancement into a lumen of a guide catheter. In some embodiments, as shown in FIG. 8A, the second end 21b of the funnel 21 is removably coupled to a second end 22b of a sleeve 22, for example by threading 24 the funnel 21 onto the second end 22b of the sleeve 22, as shown in FIGS. 8A and 8C. In some embodiments, as shown in FIGS. 9A and 9C, the threads 24 for coupling the funnel 21 to the sleeve 22, as shown in FIG. 9B, are evident using a cross-sectional view of the funnel 21 and sleeve 22. Alternatively, the funnel 21 may be coupled to the sleeve 22 by any suitable mechanism. In some embodiments, the ventricular partitioning device coupled to the delivery catheter 23 may be advanced through the funnel 21 into the sleeve 22 for loading of the ventricular partitioning device into a lumen of a guide catheter. The first end 22a of the sleeve 22 may include a stop or tapering of the sleeve, such that the ventricular partitioning device does not protrude from the first end 22a of the sleeve 22 or extend out of the first end 22a of the sleeve 22, as shown in FIGS. 8A-8C. In some embodiments, the interior of the funnel 21 and sleeve 22 may include a smooth surface, for example without flashes or burrs, such that the ventricular partitioning device is not torn or scratched during loading, unloading, and advancing.

Once, the ventricular partitioning device is advanced into the sleeve 22 from the funnel 21, the funnel 21 may be uncoupled from the sleeve 22. In some embodiments, the second end 22b of the sleeve 22 may be coupled to a guide catheter using a dilator, such that the dilator may be rotated to increase or decrease the size of the aperture in the dilator. The ventricular partitioning device may be advanced from the sleeve into the lumen of the guide catheter. In some embodiments, the delivery catheter 23 coupled to the ventricular partitioning device may be advanced through the guide catheter lumen into a heart of a patient to position the ventricular partitioning device in the heart of the patient. In some embodiments, the sleeve may be removed from the delivery catheter by any suitable mechanism after advancing the ventricular partitioning device into the lumen of the guide catheter. Alternatively, the delivery catheter may be lengthened such that the sleeve may remain on the delivery catheter while the ventricular partitioning device is being positioned in a heart of a patient.

Alternatively, in some embodiments as shown in FIGS. 10A-10D, an implant loading system for a ventricular partitioning device may further include a loader 24 comprising a lumen housing a two-piece introducer 25, referred to herein as a loader introducer pair. Instead of a two-step loading procedure, as shown in FIGS. 8A-9C, the loading procedure shown in FIGS. 10A-10D includes at least two more steps. In some embodiments, as show in FIG. 10A, the funnel 26 for loading the ventricular partitioning device into the sleeve 27 may be truncated as compared to the funnel 21 shown in FIG. 8B. Similar to FIGS. 8A and 8D, the tapered end 26b of the funnel 26 may be coupled to the second end 27b of the sleeve 27 and the ventricular partitioning device coupled to the delivery catheter may be advanced from the funnel 26 into the sleeve 27. In some embodiments, as shown in FIG. 10C, once the ventricular partitioning device is collapsed and advanced through the funnel 26 into the sleeve 27, the funnel 26 may be uncoupled from the second end 27b of the sleeve 27 and the second end 24b of the loader introducer pair 24/25 may be coupled to the second end 27b of the sleeve 27. The loader introducer pair 24/25 may be coupled to the sleeve 27 by a helical screw, latching, snapping, fastening, or any other type of coupling mechanism. The first end 24a of the loader introducer pair 24/25 may be coupled to a guide catheter, such that the lumen of the loader introducer pair is continuous with the lumen of the guide catheter. In some embodiments, as shown in FIG. 10C, the coupling mechanism may include a slot 28 on the loader 24 and a pin, knob, protrusion, or port on the guide catheter, such that the slot 28 receives the pin or port and secures the loader 24 to the guide catheter. Alternatively, the loader 24 may be coupled to the guide catheter by a helical screw, snapping, latching, or any other type of coupling mechanism.

As shown in FIG. 10C, the ventricular partitioning device may be advanced from the sleeve 27 into the loader introducer pair 24/25 and into the guide catheter. The loader 24 may be removed from the system by moving the introducer 25 and delivery catheter through a longitudinal slot 29 in the loader 24. The introducer 25 may be removed from the system by tearing or axially pulling apart the two halves 25a/25b of the introducer 25, as shown in FIG. 10D, such that the delivery catheter coupled to the ventricular partitioning device in the lumen of the guide catheter remains. In some embodiments, the sleeve 27 may remain on the delivery catheter or be removed. While two embodiments of an implant loading system are described above, any other suitable mechanism may be used and/or substituted by one skilled in the art to deliver a ventricular partitioning device to a heart of a patient.

In some embodiments, as shown in FIG. 11, a system for treating heart failure may include a ventricular partitioning device as described above, and a delivery catheter 23 having a proximal end and a distal end 23b. Further, a system for treating heart failure may include an expansion member 30 near the distal end 23b of the delivery catheter 23 configured to apply pressure to the support frame 3 of the ventricular partitioning device 1 to move the ventricular partitioning device 1 from a collapsed delivery configuration to an expanded deployed configuration, and a coupling element 31 configured to secure the expansion member 30 to the ventricular partitioning device 1 during deployment.

In some embodiments, the delivery catheter 23 may include a useable length between 120 cm and 170 cm, preferably 125 cm or 155 cm. In some embodiments, the delivery catheter 23 may include an outer diameter between 5 Fr and 14 Fr, preferably 10 Fr (3.3 mm).

In some embodiments, the expansion member 30 is coupled to the ventricular partitioning device 1 by a coupling element 31 proximal to the second ends 4b of the struts 4 of the support frame 3. In some embodiments, the coupling element 31 includes a helical screw, as shown in FIG. 11. Alternatively, in some embodiments, the coupling element 31 may include a sliding latch, lock, hook, or any other suitable mechanism. In some embodiments, the expansion member 30, for example a balloon, may be in fluid communication with a lumen in the shaft of the delivery catheter 23, such that inflation fluid may be delivered to the interior of the expansion member 30 to inflate the balloon. Alternatively, the balloon may be inflated by a gas, gel, or any other material. The balloon, once inflated, may include a diameter between 30 mm and 45 mm, preferably more than or equal to 32 mm.

In some embodiments, the ventricular partitioning device 1 radially expands in the ventricle once delivered to the ventricle. The expansion member 30, coupled to the ventricular partitioning device 1 by a coupling element 31, may be inflated at the distal end of the delivery catheter 23 to fully expand the ventricular partitioning device 1 within the ventricle and to facilitate anchoring the struts 4 of the ventricular partitioning device to an interior wall of the ventricle. Alternatively, in some embodiments, the ventricular partitioning device 1 may expand and anchor sufficiently without the use of the expansion member 30. In some embodiments, rotation of the delivery catheter 23 coupled to the ventricular partitioning device 1 may remove the expansion member 30 and delivery catheter 23 from the ventricular partitioning device 1.

In some embodiments, as shown in FIG. 12, a method of delivering a ventricular partitioning device comprises positioning with a delivery catheter an expandable partitioning device near an apex of a patient's ventricle, such that the expandable partitioning device includes a membrane coupled to a plurality of expandable struts S100; expanding an expansion member coupled to the partitioning device to apply pressure to the plurality of expandable struts to expand the partitioning device S110; and removing the expansion member from the partitioning device to deploy the partitioning device S120. In some embodiments, a method of delivering a ventricular partitioning device may further include loading the partitioning device into a guide catheter through a funnel and a sleeve. In some embodiments, a method of delivering a ventricular partitioning device may further include uncoupling a coupling element from the partitioning device to release the partitioning device from the delivery catheter. In some embodiments, a method of delivering a ventricular partitioning device may further include positioning a delivery sheath over the partitioning device to collapse the partitioning device for removal or redeployment of the partitioning device.

Manufacturing

As described above and as shown in FIGS. 6A and 6B, the struts 4 of the support frame 3 of a ventricular partitioning device are cut, for example, by a laser, from a metal tube, for example Nitinol. In some embodiments, a method for securing a membrane 5 to struts 4 of a support frame 3 includes providing the support frame 3 including a plurality of struts 4; positioning the support frame 3 within a first platen structure having a male shaping portion and a second platen structure having a female shaping portion; positioning a membrane, for example a polymeric sheet, on the support frame 3 within the first and second platen structures; pressing the first and second platen structures together; and heating the first and second platen structures housing the support frame 3 and the polymeric sheet to fuse the polymeric sheet to the support frame. In some embodiments, fusion may occur by heating and reforming of the thermoplastic material to the polymeric sheet.

In some embodiments, positioning the support frame 3 within a first platen structure includes slidably disposing tubes over the struts 4 of the support frame 3 and positioning the support frame 3 in the female platen structure on top of a membrane 5, such that the membrane 5 is sandwiched between the female platen and the support frame 3. In some embodiments, the tube disposed over the struts 4 of the support frame 3 may include a thermoplastic material or any other suitable material. In some embodiments, the membrane 5 includes a centrally located aperture configured to receive the hub 17 of the struts 4 of the support frame 3. In some embodiments, a second membrane may be positioned on top of the support frame, forming a bilaminar structure. A male platen may be positioned on the membrane 5 and support frame 3 on the female platen structure, such that the male and female platens are coupled and may be heated and pressed to couple the membrane 5 to the support structure 3. Alternatively, in some embodiments, the membrane 5 and support frame 3 may first be positioned in a male platen and the female platen may be secondarily positioned on the male platen and heated and pressed to couple the membrane 5 to the support structure 3.

In some embodiments, pressing and heating the male and female platens together may include pressing, clamping, compaction plus sintering, hot isostatic pressing, compression molding, and/or any other method known to one skilled in the art. The melting point of the thermoplastic material is lower than that of the membrane material, for example, ePTFE, such that the application of heat and pressure, as detailed above, is sufficient to melt the thermoplastic material but does not cause melting of the ePTFE membrane.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other EMBODIMENTS not specifically described herein, will be apparent to those of skill in the art upon reviewing the above description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
loading an expandable implant into a catheter for delivery to a heart utilizing an implant loading system, the implant loading system including:
a funnel having a flared first end and a second end, wherein the flared first end comprises a tapering receptacle for receiving and collapsing the expandable implant, and a second portion at the second end comprises a lumen, the second end including a coupling element for removably coupling the funnel to a sleeve, and
a sleeve configured to be removably coupled to the second end of the funnel and having a coupling element located in a center portion of the sleeve for mating with the coupling element at the second end of the funnel, the sleeve including a tubular portion distal to the coupling element of the sleeve that is configured to be positioned within the second portion of the funnel.

2. The method of claim 1, wherein the lumen of the second portion has a first diameter, and the sleeve has a lumen with a second diameter that is less than the first diameter.

3. The method of claim 2, wherein the tubular portion of the sleeve distal to the coupling element of the sleeve has the second diameter.

4. The method of claim 1, wherein the tubular portion of the sleeve distal to the coupling element of the sleeve has a lumen that is configured to receive the expandable implant from the funnel.

5. The method of claim 1, wherein the sleeve includes a tubular portion proximal to the coupling element of the sleeve.

6. The method of claim 1, wherein the tubular portion of the sleeve distal to the coupling element of the sleeve extends distal from the second end of the funnel when the funnel and the sleeve are coupled together.

7. The method of claim 1, wherein an interior of the funnel includes a smooth surface.

8. The method of claim 1, wherein the coupling element of the sleeve is positioned upon an outer surface of the sleeve.

9. The method of claim 1, wherein the coupling element of the funnel is positioned upon an interior surface of the funnel.

10. The method of claim 1, further comprising:
collapsing the expandable implant utilizing the funnel; and
advancing the expandable implant into the tubular portion of the sleeve.

11. The method of claim 1, further comprising:
collapsing the expandable implant utilizing the funnel; and
advancing the expandable implant into a lumen of the catheter.

12. The method of claim 1, further comprising coupling the sleeve with the second end of the funnel.

13. The method of claim 1, further comprising mating the coupling element of the sleeve with the coupling element at the second end of the funnel.

14. The method of claim 1, further comprising positioning the tubular portion of the sleeve within the second portion of the funnel.

15. The method of claim 1, further comprising uncoupling the sleeve from the second end of the funnel.

16. The method of claim 1, further comprising expanding the expandable implant within the heart.

17. The method of claim 1, further comprising releasing the expandable implant from the catheter.

18. The method of claim 1, further comprising uncoupling a coupling element from the expandable implant to release the expandable implant from the catheter.

19. The method of claim 1, wherein the expandable implant is for treating cardiac dysfunction.

20. The method of claim 1, further comprising collapsing a support frame of the expandable implant utilizing the funnel.

* * * * *